US012080428B1

(12) United States Patent
Syed et al.

(10) Patent No.: US 12,080,428 B1
(45) Date of Patent: Sep. 3, 2024

(54) MACHINE INTELLIGENCE-BASED PRIORITIZATION OF NON-EMERGENT PROCEDURES AND VISITS

(71) Applicant: Health at Scale Corporation, San Jose, CA (US)

(72) Inventors: Zeeshan Syed, Cupertino, CA (US); Devendra Goyal, San Francisco, CA (US); Zahoor Elahi, Plano, TX (US)

(73) Assignee: Health at Scale Corporation, San Jose, CA (US)

( * ) Notice: Subject to any disclaimer, the term of this patent is extended or adjusted under 35 U.S.C. 154(b) by 294 days.

(21) Appl. No.: 17/472,455

(22) Filed: Sep. 10, 2021

Related U.S. Application Data

(60) Provisional application No. 63/076,826, filed on Sep. 10, 2020.

(51) Int. Cl.
*G16H 50/20* (2018.01)
*G06Q 40/08* (2012.01)
(Continued)

(52) U.S. Cl.
CPC ............ *G16H 50/20* (2018.01); *G06Q 40/08* (2013.01); *G16H 10/60* (2018.01); *G16H 40/20* (2018.01); *G16H 50/30* (2018.01); *G16H 50/70* (2018.01)

(58) Field of Classification Search
CPC ........ G16H 50/20; G16H 10/60; G16H 40/20; G16H 50/30; G16H 50/70; G06Q 40/08
See application file for complete search history.

(56) References Cited

U.S. PATENT DOCUMENTS 7,191,150 B1 3/2007 Shao
7,853,456 B2 12/2010 Soto et al.
(Continued)

FOREIGN PATENT DOCUMENTS

CA 2560934 A1 11/2005
CA 2715825 A1 8/2009
(Continued)

OTHER PUBLICATIONS

Bretthauer, K. M., & Cote, M. J. (1998). A model for planning resource requirements in health care organizations. Decision Sciences, 29(1), 243-270. Retrieved from https://search.proquest.com/docview/198106120?accountid=14753 (Year: 1998).
(Continued)

*Primary Examiner* — Meredith A Long
(74) *Attorney, Agent, or Firm* — Morrison & Foerster LLP

(57) ABSTRACT

Embodiments of the present disclosure include systems and methods for generating a medical recommendation. Methods according to the present disclosure include receiving patient data associated with a first patient and receiving second patient data associated with a second patient. The methods further include inputting the first patient data and the second patient data into a trained machine-learning model to determine a first set of one or more risk values for the first patient and a second set of one or more risk values for the second patient. The methods further include comparing the first set of one or more risk values and the second set of one or more risk values to determine a priority for distributing care to the first patient and the second patient. In accordance with the determination that the first patient has priority, the system can generate a medical recommendation.

25 Claims, 18 Drawing Sheets

(51) Int. Cl.

| | |
|---|---|
| ***G16H 10/60*** | (2018.01) |
| ***G16H 40/20*** | (2018.01) |
| ***G16H 50/30*** | (2018.01) |
| ***G16H 50/70*** | (2018.01) |

(56) References Cited

U.S. PATENT DOCUMENTS 8,417,541 B1 4/2013 Kramer
8,548,937 B2 10/2013 Saigal et al.
9,996,666 B1 6/2018 Wilson
10,923,231 B2 2/2021 Kelly
10,943,676 B2 3/2021 Farooq et al.
11,114,204 B1 9/2021 Guttag et al.
11,468,998 B2 10/2022 Koblick
11,568,982 B1 1/2023 Guttag et al.
11,610,679 B1 3/2023 Zhan et al.
11,862,346 B1 1/2024 Boussios
2003/0135128 A1 7/2003 Suffin
2004/0107088 A1 6/2004 Budzinski
2006/0173663 A1 8/2006 Langheier
2006/0206359 A1 9/2006 Stang
2007/0088577 A1 4/2007 Carter et al.
2007/0269804 A1 11/2007 Liew
2008/0120138 A1* 5/2008 Morita .................. G16H 40/20 705/3
2009/0093689 A1 4/2009 Schuppert et al.
2009/0259550 A1 10/2009 Mihelich
2010/0184093 A1 7/2010 Donovan
2011/0082712 A1 4/2011 Eberhardt, III
2011/0295621 A1 12/2011 Farooq et al.
2011/0307426 A1* 12/2011 Syed ...................... G16H 50/30 706/12
2012/0041330 A1 2/2012 Prichep et al.
2012/0066217 A1 3/2012 Eder
2012/0095943 A1 4/2012 Yankov
2012/0109683 A1 5/2012 Ebadollahi
2012/0179002 A1 7/2012 Brunetti et al.
2013/0022953 A1 1/2013 Van Der Linden
2013/0096948 A1 4/2013 Parkinson
2013/0185096 A1 7/2013 Giusti
2013/0197925 A1 8/2013 Blue
2013/0225439 A1 8/2013 Princen et al.
2014/0058755 A1 2/2014 Macoviak
2014/0108034 A1 4/2014 Akbay
2014/0200824 A1 7/2014 Pancoska
2014/0257838 A1 9/2014 Karra
2014/0371610 A1 12/2014 Liu et al.
2015/0006456 A1 1/2015 Sudharsan
2015/0046181 A1 2/2015 Adjaoute
2015/0073943 A1 3/2015 Norris et al.
2015/0100336 A1 4/2015 Ford et al.
2015/0100349 A1 4/2015 Lacy et al.
2015/0161331 A1 6/2015 Oleynik
2015/0164453 A1 6/2015 Choi et al.
2015/0248534 A1 9/2015 Krzywicki et al.
2015/0278470 A1 10/2015 Bakker
2015/0289795 A1 10/2015 Batlle Gómez
2015/0294075 A1 10/2015 Rinaldo
2015/0317449 A1 11/2015 Eder
2015/0367145 A1 12/2015 Sjölund et al.
2016/0012202 A1 1/2016 Hu et al.
2016/0085937 A1 3/2016 Dettinger
2016/0125168 A1* 5/2016 Aagesen ................ G16H 10/60 705/3
2016/0135706 A1 5/2016 Sullivan et al.
2016/0147959 A1 5/2016 Mariottini et al.
2016/0196398 A1 7/2016 Vivero et al.
2016/0203217 A1 7/2016 Anisingaraju et al.
2016/0232310 A1 8/2016 Dunn
2016/0259883 A1 9/2016 Grinchuk et al.
2016/0378943 A1 12/2016 Vallée
2017/0073761 A1 3/2017 Harkin et al.
2017/0083682 A1 3/2017 Mcnutt
2017/0101093 A1 4/2017 Barfield, Jr. et al.
2017/0124269 A1 5/2017 Mcnair
2017/0177822 A1 6/2017 Fogel
2017/0185723 A1 6/2017 Mccallum et al.
2017/0277856 A1 9/2017 De La Torre et al.
2017/0308671 A1 10/2017 Bahrami et al.
2017/0316180 A1 11/2017 Takeda et al.
2018/0121619 A1 5/2018 Perlroth et al.
2018/0181719 A1 6/2018 Balian
2018/0182475 A1 6/2018 Cossler
2018/0211013 A1* 7/2018 Courtemanche ....... G16H 40/67
2018/0214105 A1 8/2018 Anavi et al.
2018/0271455 A1 9/2018 Zhong et al.
2019/0043606 A1 2/2019 Roots et al.
2019/0051389 A1* 2/2019 Meittunen ............. G16H 40/20
2019/0172587 A1 6/2019 Park et al.
2019/0333613 A1 10/2019 Zaidi et al.
2019/0371450 A1 12/2019 Lou et al.
2020/0020453 A1 1/2020 Yarbray
2020/0066397 A1* 2/2020 Rai ........................ G06N 20/00
2020/0074313 A1 3/2020 Sharifi Sedeh et al.
2020/0342335 A1 10/2020 Burke
2021/0020294 A1* 1/2021 Bharmi ................. G16H 50/30
2021/0035693 A1 2/2021 Mohammad et al.
2021/0043320 A1 2/2021 Malkenson
2021/0065909 A1 3/2021 Donaldson
2021/0090748 A1 3/2021 Toyoshiba et al.
2021/0098090 A1 4/2021 Thomas
2021/0118559 A1 4/2021 Lefkofsky
2021/0221404 A1 7/2021 Reiner et al.
2021/0249138 A1 8/2021 Hayashitani et al.
2021/0296000 A1* 9/2021 Shaw ..................... G16H 70/00
2022/0061746 A1* 3/2022 Lyman .................. G16H 30/20

FOREIGN PATENT DOCUMENTS

EP 3382584 A1 10/2018
EP 3500999 A1 6/2019
JP 2017174406 A 9/2017
WO 2001070094 A2 9/2001
WO 2015157576 A1 10/2015
WO 2016044514 A1 3/2016
WO 2016120955 A1 8/2016
WO 2017072651 A1 5/2017
WO 2019212005 A1 11/2019
WO 2020081609 A1 4/2020

OTHER PUBLICATIONS

Caruana, Rich. (1997). "Multitask Learning," Kluwer Academic Publishers, Manufactured in the Netherlands, Machine Learning, 35 pages.

Caruana, Rich. (May 1996). "Algorithms and Applications for Multitask Learning," School of Computer Science, Carnegie Mellon University, Pittsburgh, PA, 9 pages.

Final Office Action mailed Dec. 21, 2020, for U.S. Appl. No. 14/622,112, filed Feb. 13, 2015, nine pages.

Final Office Action mailed Dec. 26, 2018, for U.S. Appl. No. 14/809,528, filed Jul. 27, 2015, 30 pages.

Final Office Action mailed Jan. 7, 2019, for U.S. Appl. No. 14/736,470, filed Jun. 11, 2015, fifteen pages.

Final Office Action mailed Jul. 21, 2020, for U.S. Appl. No. 14/678,349, filed Apr. 3, 2015, twelve pages.

Final Office Action mailed Jul. 21, 2020, for U.S. Appl. No. 14/809,528, filed Jul. 27, 2015, twenty pages.

Final Office Action mailed Jul. 23, 2018, for U.S. Appl. No. 14/622,112, filed Feb. 13, 2015, eleven pages.

Final Office Action mailed May 3, 2018, for U.S. Appl. No. 14/678,349, filed Apr. 3, 2015, twenty one pages.

Final Office Action mailed Nov. 16, 2020, for U.S. Appl. No. 14/736,470, filed Jun. 11, 2015, eleven pages.

Non-Final Office Action mailed Aug. 17, 2021, for U.S. Appl. No. 14/622,112, filed Feb. 13, 2015, 11 pages.

Non-Final Office Action mailed Aug. 27, 2021, for U.S. Appl. No. 14/809,528, filed Jul. 27, 2015, 14 pages.

Non-Final Office Action malled Dec. 18, 2019, for U.S. Appl. No. 14/678,349, filed Apr. 3, 2015, eleven pages.

(56) References Cited

OTHER PUBLICATIONS

Non-Final Office Action mailed Feb. 26, 2018, for U.S. Appl. No. 14/736,470, filed Jun. 11, 2015, sixteen pages.
Non-Final Office Action mailed Jan. 10, 2019, for U.S. Appl. No. 14/678,349, filed Apr. 3, 2015, twenty two pages.
Non-Final Office Action mailed Jan. 29, 2020, for U.S. Appl. No. 14/809,528, filed Jul. 27, 2015, 20 pages.
Non-Final Office Action mailed Jan. 29, 2021, for U.S. Appl. No. 14/678,349, filed Apr. 3, 2015, eight pages.
Non-Final Office Action mailed Mar. 14, 2019, for U.S. Appl. No. 14/622,112, filed Feb. 13, 2015, ten pages.
Non-Final Office Action mailed Mar. 27, 2020, for U.S. Appl. No. 14/622,112, filed Feb. 13, 2015, nine pages.
Non-Final Office Action mailed Mar. 9, 2020, for U.S. Appl. No. 14/736,470, filed Jun. 11, 2015, nine pages.
Non-Final Office Action mailed May 1, 2018, for U.S. Appl. No. 14/809,528, filed Jul. 27, 2015, 25 pages.
Non-Final Office Action mailed Sep. 22, 2017, for U.S. Appl. No. 14/678,349, filed Apr. 3, 2015, thirteen pages.
Non-Final Office Action mailed Sep. 28, 2017, for U.S. Appl. No. 14/622,112, filed Feb. 13, 2015, fifteen pages.
Notice of Allowance mailed Jul. 28, 2021, for U.S. Appl. No. 14/678,349, filed Apr. 3, 2015, eleven pages.
Baechle, C., et al., "Latent topic ensemble learning for hospital readmission cost optimization," European Journal of Operational Research 281 (2020) 517-531. (Year: 2019).
Non-Final Office Action mailed Feb. 8, 2022, for U.S. Appl. No. 16/853,621, filed Apr. 20, 2020, 27 pages.
Rahimian, F., et al., "Predicting the risk of emergency admission with machine learning: Development and validation using linked electronic health records," PLOS Medicine, Nov. 20, 2018, pp. 1-18 (Year: 2018).
Brakenhoff, T. B., et al. (2018). "Investigating Risk Adjustment Methods for Health Care Provider Profiling When Observations are Scarce or Events Rare". Health Services Insights, vol. 11, 1-10, doi: http://dx.doi.org/10.1177/1178632918785133 , (Year:2018).
Final Office Action mailed Jul. 12, 2022, for U.S. Appl. No. 16/853,621, filed Apr. 20, 2020, twenty-three pages.
Final Office Action mailed May 18, 2023, for U.S. Appl. No. 16/875,835, filed May 15, 2020, fifty-five pages.
Final Office Action mailed Oct. 4, 2022, for U.S. Appl. No. 14/736,470, filed Jun. 11, 2015, thirteen pages.
Li, Xiuli et al., "Lung Nodule Malignancy Prediction Using Multi-task Convolutional Neural Network," Proc. of SPIE vol. 10134, 1013424-1 (Year: 2017).
Non-Final Office Action mailed Dec. 14, 2022, for U.S. Appl. No. 14/809,528, filed Jul. 27, 2015, fifteen pages.
Non-Final Office Action mailed Jan. 18, 2023, for U.S. Appl. No. 17/392,086, filed Aug. 2, 2021, nineteen pages.
Non-Final Office Action mailed Jul. 20, 2023, for U.S. Appl. No. 17/398,931, filed Aug. 10, 2021, twenty pages.
Non-Final Office Action mailed Jul. 27, 2022, for U.S. Appl. No. 16/875,835, filed May 15, 2020, forty-eight pages.
Non-Final Office Action mailed Mar. 18, 2022, for U.S. Appl. No. 14/736,470, filed Jun. 11, 2015, fourteen pages.
Notice of Allowance mailed Feb. 2, 2023, for U.S. Appl. No. 16/853,621, filed Apr. 20, 2020, sixteen pages.
Notice of Allowance mailed Nov. 7, 2022, for U.S. Appl. No. 14/622,112, filed Feb. 13, 2015, nine pages.
Notice of Allowance mailed Sep. 6, 2022, for U.S. Appl. No. 14/622,112, filed Feb. 13, 2015, nine pages.
Ruder, Sebastian. "An Overview of Multi-Task Learning in Deep Neural Networks," https://ruder.io/multi-task/ (Year: 2017).
Tan, Kar Way. "Dynamic Queue Management for Hospital Emergency Room Services." Order No. 10169843 Singapore Management University (Singapore), 2013. Ann Arbor: ProQuest. Web., Aug. 25, 2022. (Year: 2013).
Final Office Action mailed Feb. 8, 2024, for U.S. Appl. No. 17/398,931, filed Aug. 10, 2021, ten pages.
Herrete, Emily et al. (Jun. 1, 2015). "Data Resource Profile: Clinical Practice Research Datalink (CPRD) (English)", International Journal of Epidemiology, 44(3), 827-836, (Year: 2015).
Modin, Sonja et al. (Jun. 22, 2009). "Family physicians' effort to stay in charge of the medical treatment when patients have home care by district nurses. A grounded theory study (English)", BMC Family Practice, 10, 45, (Year-2009).
Non-Final Office Action mailed Feb. 6, 2024, for U.S. Appl. No. 17/472,383, filed Sep. 10, 2021, thirty-one pages.
Non-Final Office Action mailed Feb. 7, 2024, for U.S. Appl. No. 14/809,528, filed Jul. 27, 2015, seventeen pages.
Non-Final Office Action mailed Sep. 27, 2023, for U.S. Appl. No. 16/875,835, filed May 15, 2020, seventy-three pages.
Alvarez Bustins, et al., "Profile of Osteopathic practice in Spain: results from a standardized data collection study (English)", BMC Complementary and Alternative Medicine, 18, 129, Apr. 11, 2018 (Year: 2018).
Notice of Allowance mailed May 1, 2024, for U.S. Appl. No. 17/398,931, filed Aug. 10, 2021, thirteen pages.
Subhra Shriti Mishra et al. "IoT Health care Monitoring and Tracking: A Survey (English)", 2019 3rd International Conference on Trends in Electronics and Informatics (ICOEI) (pp. 1052-1057), Oct. 25, 2019 (Year: 2019).

* cited by examiner

HISTORICAL DATA 102

PATIENT 1 DATA 210 . . . PATIENT N DATA 220

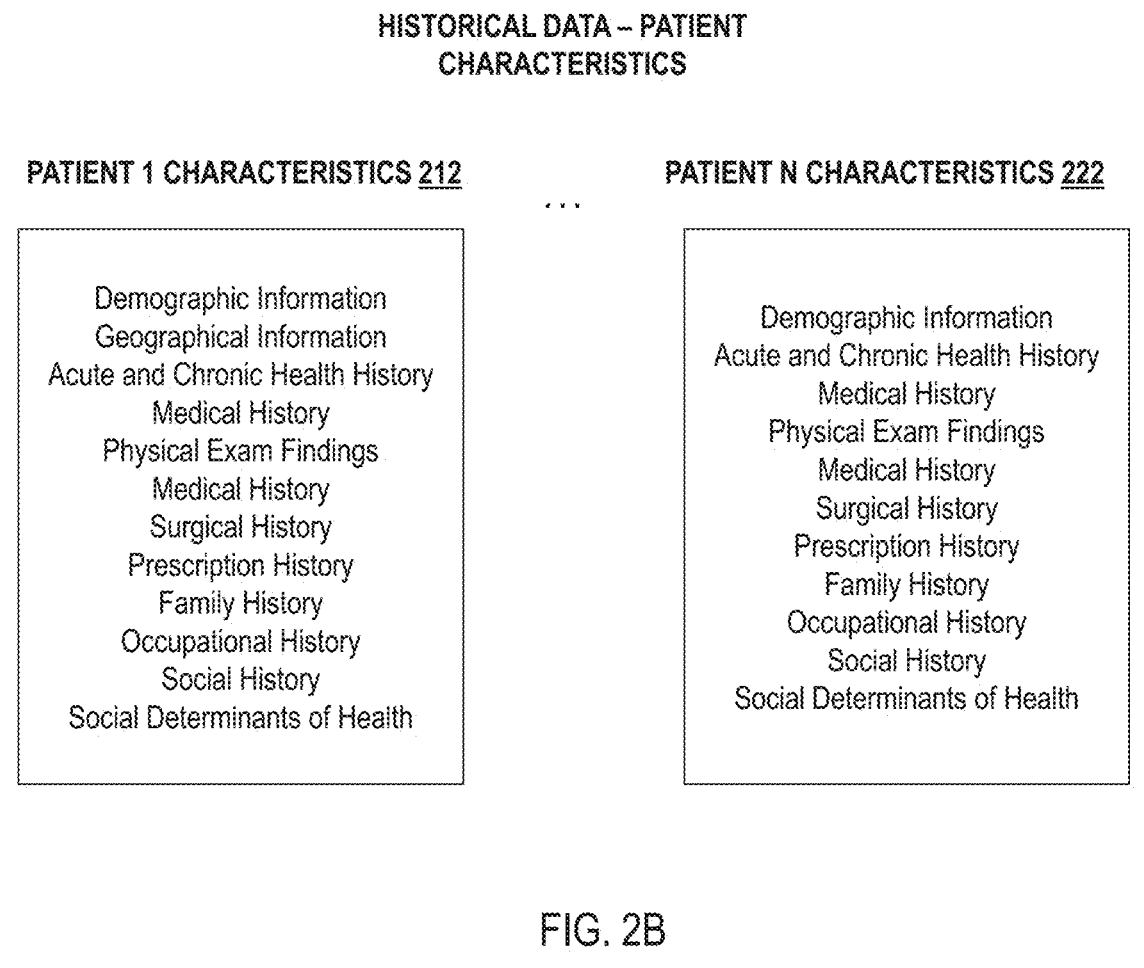

HISTORICAL DATA – PATIENT CHARACTERISTICS

PATIENT 1 CHARACTERISTICS 212

Demographic Information
Geographical Information
Acute and Chronic Health History
Medical History
Physical Exam Findings
Medical History
Surgical History
Prescription History
Family History
Occupational History
Social History
Social Determinants of Health

. . .

PATIENT N CHARACTERISTICS 222

Demographic Information
Acute and Chronic Health History
Medical History
Physical Exam Findings
Medical History
Surgical History
Prescription History
Family History
Occupational History
Social History
Social Determinants of Health

FIG. 2B

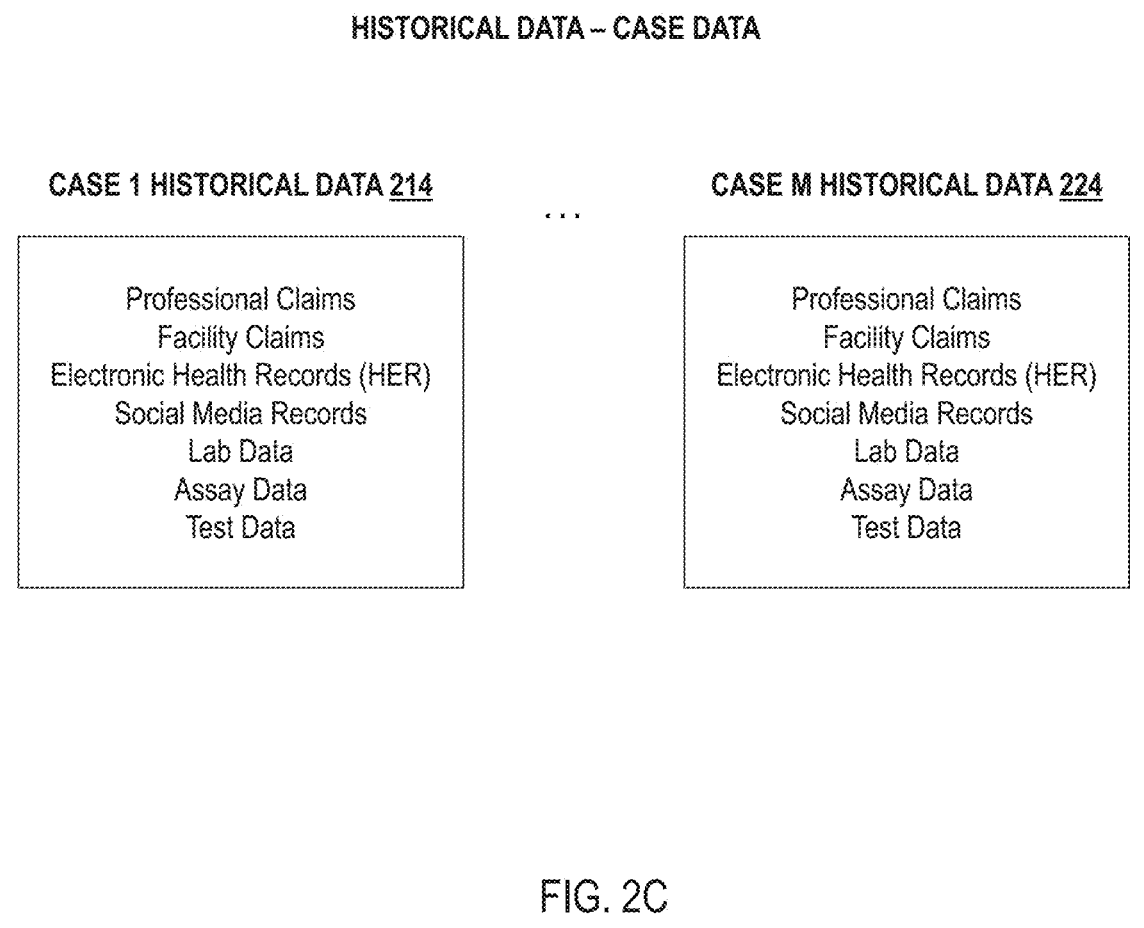

HISTORICAL DATA – CASE DATA

CASE 1 HISTORICAL DATA 214

Professional Claims
Facility Claims
Electronic Health Records (HER)
Social Media Records
Lab Data
Assay Data
Test Data

. . .

CASE M HISTORICAL DATA 224

Professional Claims
Facility Claims
Electronic Health Records (HER)
Social Media Records
Lab Data
Assay Data
Test Data

FIG. 2C

PREDICT RISK VALUE 140

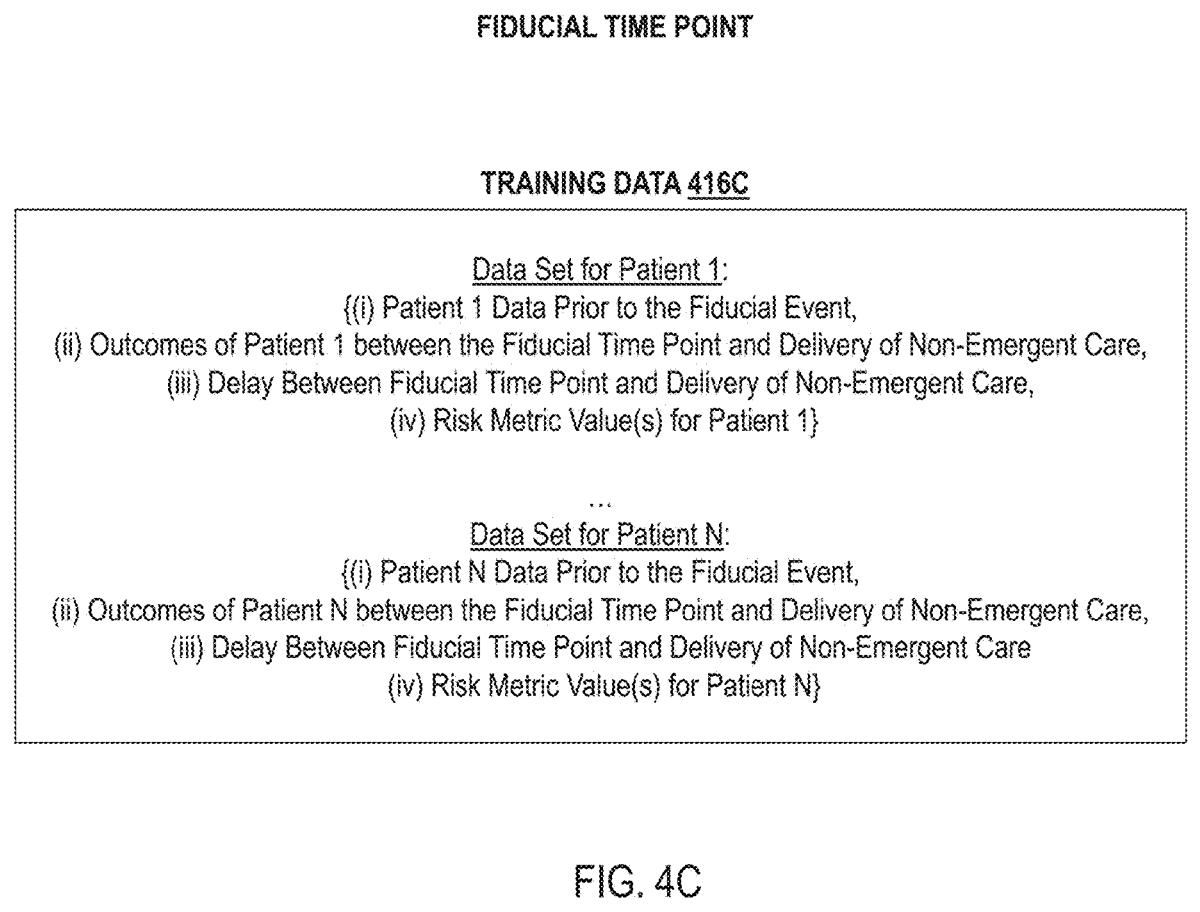

FIDUCIAL TIME POINT

TRAINING DATA 416C

Data Set for Patient 1:
{(i) Patient 1 Data Prior to the Fiducial Event,
(ii) Outcomes of Patient 1 between the Fiducial Time Point and Delivery of Non-Emergent Care,
(iii) Delay Between Fiducial Time Point and Delivery of Non-Emergent Care,
(iv) Risk Metric Value(s) for Patient 1}

...

Data Set for Patient N:
{(i) Patient N Data Prior to the Fiducial Event,
(ii) Outcomes of Patient N between the Fiducial Time Point and Delivery of Non-Emergent Care,
(iii) Delay Between Fiducial Time Point and Delivery of Non-Emergent Care
(iv) Risk Metric Value(s) for Patient N}

FIG. 4C

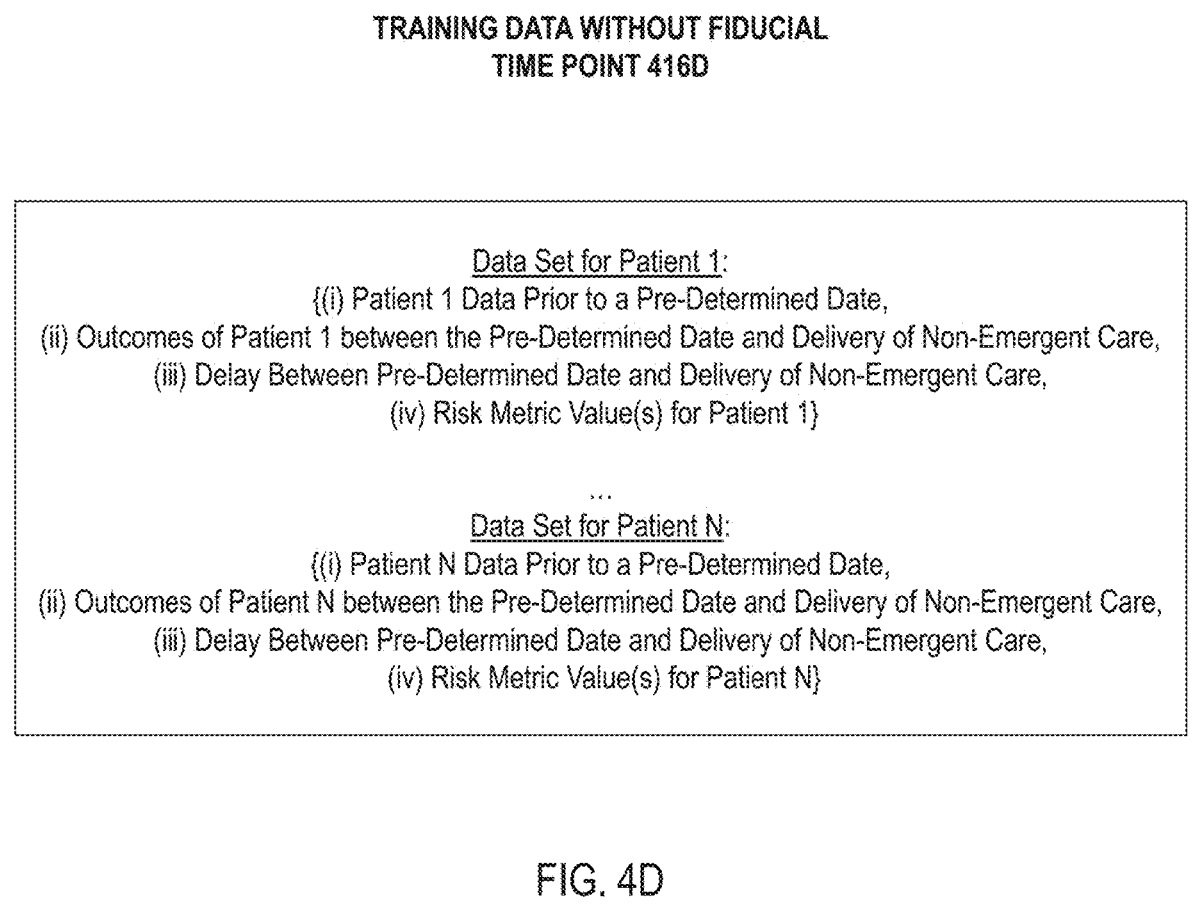

TRAINING DATA WITHOUT FIDUCIAL
TIME POINT 416D

Data Set for Patient 1:
{(i) Patient 1 Data Prior to a Pre-Determined Date,
(ii) Outcomes of Patient 1 between the Pre-Determined Date and Delivery of Non-Emergent Care,
(iii) Delay Between Pre-Determined Date and Delivery of Non-Emergent Care,
(iv) Risk Metric Value(s) for Patient 1}

...

Data Set for Patient N:
{(i) Patient N Data Prior to a Pre-Determined Date,
(ii) Outcomes of Patient N between the Pre-Determined Date and Delivery of Non-Emergent Care,
(iii) Delay Between Pre-Determined Date and Delivery of Non-Emergent Care,
(iv) Risk Metric Value(s) for Patient N}

FIG. 4D

PRIORITIZE NON-EMERGENT CARE
150

1000

MACHINE INTELLIGENCE-BASED PRIORITIZATION OF NON-EMERGENT PROCEDURES AND VISITS

CROSS-REFERENCE TO RELATED APPLICATIONS

This application claims priority to and the benefit of U.S. Provisional Patent Application No. 63/076,826, filed Sep. 10, 2020, the disclosure of which is herein incorporated by reference in its entirety.

FIELD OF DISCLOSURE

The present disclosure relates generally to machine-learning techniques, and more specifically to machine-learning techniques for prioritizing medical procedures and visits.

BACKGROUND

The prioritization of non-emergent care is an essential healthcare challenge in the presence of resource constraints within the health system, especially in light of a shortage of skilled human resources or equipment and other contextual factors that make access to health care resources a challenge. For example, in the U.S., the 2017 Survey of Physician Appointment Wait Times and Medicare and Medicaid Acceptance Rates found that the average wait time to schedule a first-time appointment with a physician was 24 days (a 30% increase from 2014) with patients in Boston experiencing an average of 52 days. For some specialties, the wait was even longer; in Philadelphia, for example, the wait time to see a dermatologist was 78 days. In addition to this limit on skilled human resources or equipment, the COVID-19 pandemic has given rise to another example of the need to prioritize non-emergent care. Confronted with the concerns that existing resources may need to be re-positioned to focus on the rising number of COVID-19 cases and a desire to minimize exposure to patients, hospital administrators responded by almost entirely shutting down elective surgeries and care. For some patients with cancer, cardiac disease and other serious conditions, this response had disastrous effects for health system finances and outcomes for patients where the deferral of non-emergent care led to significant progression of mortality and morbidity that could otherwise have been reduced with more intelligent decisions about which elective care to defer or not defer.

BRIEF SUMMARY

Embodiments of the present disclosure can predict how risk varies across patients for delays in non-emergent procedures and visits for evaluation and management purposes (e.g., visits for preventative, regular, diagnostic etc. care) and can use this information about risk variations across patients to prioritize non-emergent procedures and visits. In some embodiments, the prioritization is accomplished using machine intelligence to model the risk trajectories of patients that are in the queue to receive non-emergent care over time, as a way to predict the variable risk to patients if non-emergent care is delayed.

In the setting of pandemics such as COVID-19, where delays in non-emergent care may periodically be needed to reduce exposure to patients, embodiments of the present disclosure can distinguish patients who should continue to receive non-emergent care (i.e., where the risk of exposure and infection is less than the risk of delaying an essential visit for a condition that might worsen and cause significant mortality and morbidity) from patients for whom non-emergent care should be deferred.

In other settings of resource constraints, where limitations on skilled human or capital equipment resources make it impossible to deliver care to all patients in a timely manner, embodiments of the present disclosure can distinguish patients who are at highest risk and most in need of urgent care from those who are more likely to be able to wait for care to be delivered due to lower risk.

Embodiments of the present disclosure include systems and methods for using machine-learning to generate a medical recommendation. For example, methods according to the present disclosure can include receiving, by one or more processors, first patient data associated with a first patient and receiving, by one or more processors, second patient data associated with a second patient. The methods can further include inputting the first patient data into a trained machine-learning model to determine a first set of one or more risk values for the first patient and inputting the second patient data into the first trained machine-learning model to determine a second set of one or more risk values for the second patient. The methods can further include comparing the first set of one or more risk values and the second set of one or more risk values to determine a priority for distributing non-emergent care to the first patient and the second patient. In accordance with the determination that the first patient has priority, the methods can further generate a medical recommendation based on the priority.

In one or more embodiments, a risk value of the first set of one or more risk values corresponds to: a probability of an outcome within a time frame, a number of events of the outcome within a time frame, a time to a first occurrence of the outcome, a time-series of outcome events as a function of time, or the time-series of outcome probabilities as a function of time.

In one or more embodiments, the method can further include automatically scheduling an appointment for the first patient. In one or more embodiments, the method can further include sending a notification to a provider, wherein the notification a medical recommendation for distributing care to the first patient based on the priority. In one or more embodiments, the method can further include displaying the medical recommendation to a provider. In one or more embodiments, the method can further include sending a notification to the first patient, wherein the notification recommends next steps for distributing care to the first patient.

In one or more embodiments, generating the medical recommendation comprises identifying a first treatment for the first patient. In one or more embodiments, the method can further include sending the second set of one or more risk values to the provider, wherein generating the medical recommendation comprises identifying a second treatment for the second patient. In one or more embodiments, the electronic health records of the first patient is updated to include the priority and the first risk value. In one or more embodiments, the method can further include selecting the model from a plurality of trained machine learning models based on one or more events that have occurred to the first patient and the second patient. In one or more embodiments, the method can further include determining an updated first set of risk values and an updated second set of risk values at regular intervals, and determining an updated priority based on the updated first set of risk values and the updated second set of risk values.

In one or more embodiments, patient data comprises patient characteristics, care service records, or a combination thereof. In one or more embodiments, the patient characteristics can comprise demographic information, acute and chronic health history, history and physical exam findings, medical history, surgical history, prescription history, family history, occupational history, social history, review of systems, social determinants of health, or a combination thereof. In one or more embodiments, the care service records can include a medical professional claim, a medical facility claim, a pharmacy claim, electronic health records, self-reported outcomes, digital health records, social media records, data from laboratory test, or a combination thereof. In one or more embodiments, the machine-learning model is configured to receive a patient-specific dataset and output a third set of risk values indicative of a health of the corresponding patient in the absence of non-emergent care.

In one or more embodiments, the first machine-learning model is trained by: receiving, by one or more processors, training data including: a plurality of patient-specific datasets for a plurality of patients for a first time period and a set of estimated risk values for the plurality of patients for a second time period, after the first time period, and training the first machine-learning model based on the training data. In one or more embodiments, the training data includes a fiducial time point. In one or more embodiments, the method can further include modifying, by the one or more processors, the received patient data to obtain respective augmented patient data, and wherein inputting the patient data into the first trained machine-learning model comprises inputting the augmented patient data into the first trained machine-learning model.

Embodiments of the present disclosure can further include systems generating a medical recommendation. In one or more embodiments, the systems can include one or more processors, a memory, and one or more programs. In some embodiments, the one or more programs are stored in the memory and configured to be executed by the one or more processors. The one or more programs can include instructions for: receiving, by one or more processors, first patient data associated with a first patient, receiving, by one or more processors, second patient data associated with a second patient, inputting the first patient data into a trained machine-learning model to determine a first set of one or more risk values for the first patient, inputting the second patient data into the first trained machine-learning model to determine a second set of one or more risk values for the second patient, comparing the first set of one or more risk values and the second set of one or more risk values to determine a priority for distributing non-emergent care to the first patient and the second patient, and in accordance with the determination that the first patient has priority, generating a medical recommendation based on the priority.

Embodiments of the present disclosure include non-transitory computer-readable storage medium storing one or more programs, the one or more programs comprising instructions. In some embodiments, the instructions, when executed by one or more processors of one or more electronic devices, cause the electronic devices to: receive, by one or more processors, first patient data associated with a first patient, receive, by one or more processors, second patient data associated with a second patient, input the first patient data into a trained machine-learning model to determine a first set of one or more risk values for the first patient, input the second patient data into the first trained machine-learning model to determine a second set of one or more risk values for the second patient, compare the first set of one or more risk values and the second set of one or more risk values to determine a priority for distributing non-emergent care to the first patient and the second patient, and in accordance with the determination that the first patient has priority, generate a medical recommendation based on the priority.

DESCRIPTION OF THE FIGURES

FIGS. 2A-2C illustrate exemplary patient data, in accordance with some embodiments of this disclosure.

FIGS. 4C-4D illustrate exemplary training data, in accordance with some embodiments of this disclosure.

DETAILED DESCRIPTION

Figure 1:
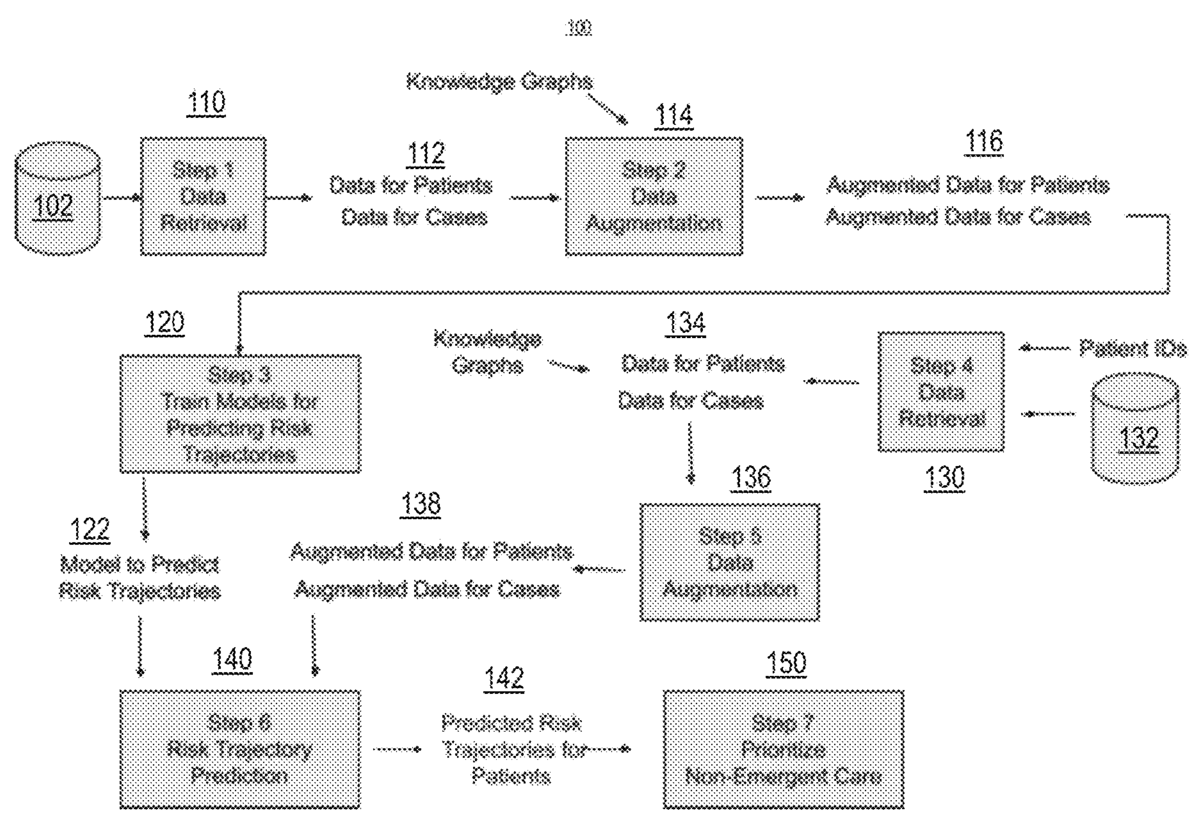
FIG. 1 illustrates an exemplary process for prioritizing medical visits and procedures, in accordance with some embodiments.

The prioritization of non-emergent care is an essential healthcare challenge in the presence of resource constraints within the health system. Existing approaches to this problem have generally focused on a combination of one or more of: (i) shutting down all non-emergent care (e.g., in the setting of COVID-19), which disregards the need for some patients experiencing significant mortality and morbidity if their care is deferred; (ii) prioritizing cases in a first-come first-served manner, which fails to appreciate the urgency for some patients to receive care relative to others; (iii) exercising subjective clinical judgment, which is highly variable and error prone; and (iv) using simple risk scores and simple guidelines to risk-stratify patients, which are typically defined with regards to a handful of attributes and fail to account for the wide variation in patient risk according to tens of thousands of diagnostic, procedural, pharmacologic, history and physical exam etc.-based parameters, are often based on clinical trials data with stringent inclusionary and exclusionary criteria that render them inadequate for broad population use, only consider one or a small number of outcomes and fail to provide a holistic assessment of risk, and are usually based on scoring patients for risk rather than the risk due to deferral of elective care.

Embodiments of the present disclosure can prioritize patients by modeling how patient risk will change over time in the absence of non-emergent care being delivered and use this modeling to predict the risk trajectories of patients to prioritize their non-emergent care. Using machine intelligence, some embodiments develop models that can factor in tens of thousands of patient attributes to predict time-varying risk for multiple outcomes. Furthermore, using machine intelligence, some embodiments can build these models off observational data for representative populations, where partial knowledge of outcomes is available over a future period (i.e., variable amounts of data are available for patients in the absence of non-emergent care for modeling time-varying risk for delays in non-emergent care delivery). Embodiments of the present disclosure therefore provides a machine intelligence-based data-driven approach for prioritization that is predictive, accurate, quantitative and deeply personalized and can model the time-varying risk trajectories of patients if they do not receive non-emergent care while dealing with the issues above. In particular, the machine intelligence-based approach can model high-dimensional patient data and address the challenges associated with partial knowledge of outcomes over a future period through the ability to deal with censored data and model time-varying hazard and survival.

Embodiments of the present disclosure have short-term significance due to the COVID-19 pandemic and has longer-term significance due to the aging population and shortfall in care providers, where the shortfall is geographical as well as associated with certain specialties of which primary care is the most important. This shortfall will mean that in many cases the frontline care team is and will be the health care staff who is not necessarily a medical practitioner. This support staff is part of the workflow of health care and is deeply involved with provider referrals and frontline appointment scheduling. These health care workers should not be burdened with making judgements on prioritization in the currently prevalent ad-hoc manner. Embodiments of the present disclosure aid these workers as well as the providers in prioritization of care.

With a knowledge of the anticipated needs of care services for one or more patients and the prioritization of these anticipated needs, some embodiments of the present disclosure also cause or trigger the action to be taken by health plans and provider systems of prioritizing patients; and to select optimal prioritization to deliver care. This action is implemented through the employment of a multi-modal approach to ensure that the prioritization recommendation is presented to the decision maker at the point of decision in real-time.

In one mode, some embodiments can be used in a direct to health plan and provider mode to present the prioritization recommendation. In this mode the recommendation is part of health plan care manager facing applications or provider system (provider and care team) facing applications (websites, mobile applications, call centers) that health plans and provider organization use or may use to manage, prioritize, schedule and communicate with patients and inform them of information related to their health care including care prioritization.

In another mode, outputs of the models and the recommendation of prioritization can be provided to health plans and provider systems at a timed cadence (daily, weekly, monthly etc.) to highlight high priority patients for the health plans and provider systems to manage and then use to communicate with the patients.

In another mode, embodiments of the present disclosure can serve up prioritization recommendations directly to providers or care team members who are working to select further care and evaluation of a patient. In this mode, the recommendation is available to the health plan care manager via deep integration to the health plan's care management portal or application and it is available to the provider and provider care teams via deep integration with the provider's Electronic Health Record (EHR) application. The EHR facing integration is part of the provider workflow that allows seamless integration and use by simple clicks and drop down menus to receive prioritization recommendations in real-time for immediate action. All these modes of representing the prioritization to health plans and providers (via direct to at the point of decision care team member or via a timed cadence or built into the provider EHR for use by all provider team members) are a key elements to the use of prioritization across the spectrum of when scheduling and next step care decisions are being taken.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including." "comprises," and/or "comprising." when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1 illustrates an exemplary process for prioritizing medical visits and procedures, in accordance with some embodiments. Process 100 is performed, for example, using one or more electronic devices implementing a software platform. In some examples, process 100 is performed using a client-server system, and the blocks of process 100 are divided up in any manner between the server and a client device. In other examples, the blocks of process 100 are divided up between the server and multiple client devices. In other examples, process 100 is performed using only a client device or only multiple client devices. In process 100, some blocks are, optionally, combined, the order of some blocks is, optionally, changed, and some blocks are, optionally, omitted. In some examples, additional steps may be performed in combination with the process 100. Accordingly, the operations as illustrated (and described in greater detail below) are exemplary by nature and, as such, should not be viewed as limiting.

Figure 2A:
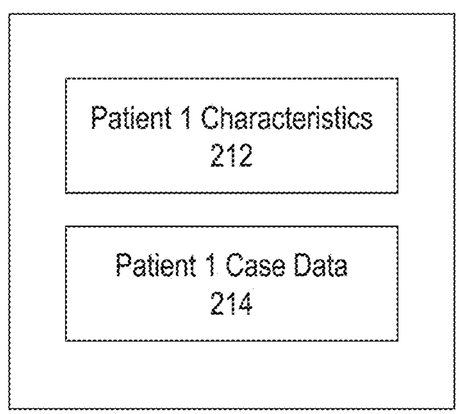
Figure 2A:
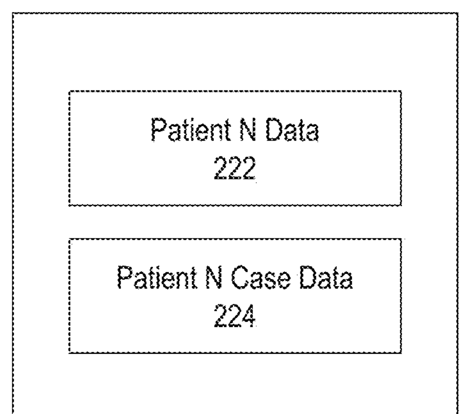

At Block 110, an exemplary system (e.g., one or more electronic devices) retrieves historical data 102 (e.g., from one or more databases of historical records) for previously serviced patients and cases. FIG. 2A illustrates exemplary historical data 102 for patients 1-N obtained from one or more databases. As shown in the figure, the historical data for each patient can include patient data (e.g., patient characteristics 212, 222) and case data (e.g., case data 214, 224). In some embodiments, the data comprises a dataset for each patient or case. Each dataset can include one or more vectors or tensors. The vectors and tensors can comprise values that are numeric (e.g., age), categorical (e.g., male/female), or ordinal (e.g., poor, fair, good, excellent health).

FIG. 2B illustrates exemplary historical patient characteristics 212, 222, according to embodiments of the present disclosure. In some embodiments, the data can include characteristics of patients across multiple years 1-Y (e.g., demographic information such as age and sex; geographical information; acute and chronic health history; history and physical exam findings; past medical, surgical and prescription history; family history; occupational history; social history; review of systems; social determinants of health etc.). A skilled artisan will understand that examples of types of historical patient characteristics 212, 222 are exemplary and that some types of data can be omitted or additional types of data can be included without departing from the scope of this disclosure. For example, for a patient John Doe, the historical data can include: age=73 years, sex=male, location (zip3)=021, acute condition=pneumonia, chronic comorbidities=[hypertension, diabetes, hypothyroidism], functional status=independent, prescription history=[Lasix, Metformin], etc.

FIG. 2C illustrates exemplary historical case data 214, 224, according to embodiments of the present disclosure. In some embodiments, the case data can include past case records for non-emergent care across multiple years 1-Y (e.g., professional, facility and pharmacy claims; electronic health records; self-reported outcomes; digital health records; social media records; data from labs, assays, and other tests; etc.). A skilled artisan will understand that examples of types of historical case data 214, 224 are exemplary and that some types of data can be omitted or additional types of data can be included without departing from the scope of this disclosure.

Figure 3:
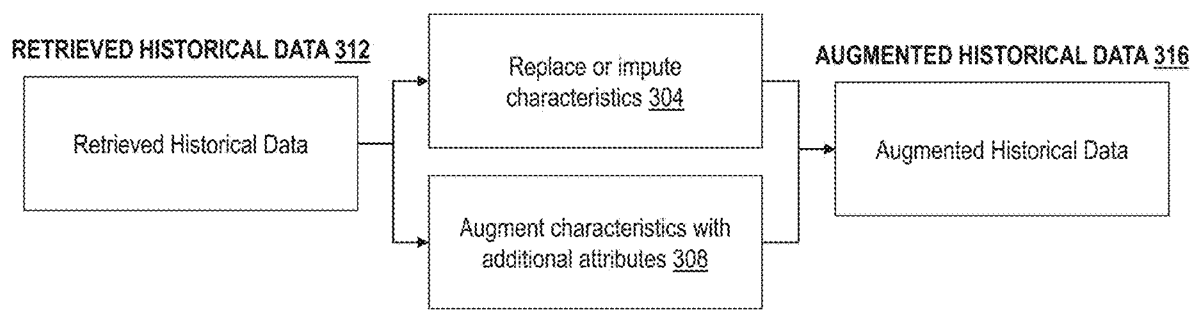
FIG. 3 illustrates an exemplary process for determining prioritization of care services provided to a patient, in accordance with some embodiments of this disclosure.

At Block 114, the system augments data for providers and previously serviced patients and cases. FIG. 3 illustrates data augmentation at Block 114 according to embodiments of the present disclosure. In some embodiments, the system augments the retrieved historical data 312 (e.g., data 112 retrieved in Block 110) by either: at Block 304, replacing or imputing characteristics that were otherwise attempted to be retrieved for patients and cases, but were missing or found to be noisy; or at Block 308, augmenting the characteristics retrieved for providers, patients and cases with additional attributes. For example, the retrieved historical data 312, e.g., corresponding to patient data 102, can be augmented via Block 304 or Block 308 to obtain augmented historical data 316. In some examples, data can be augmented via both Blocks 304 and 308, e.g., by both replacing or imputing characteristics that were otherwise attempted to be retrieved for patients and cases, but were missing or found to be noisy and augmenting the characteristics retrieved for patients and cases with additional attributes. As used herein the process of replacing, imputing, and/or augmenting characteristics can refer generally to augmenting characteristics of the retrieved patient data, e.g., retrieved historical patient data 112, 312.

In some examples, the process of replacing or imputing characteristics at Block 312 can be performed under various assumptions of missingness such as, but not limited to, missing completely at random (MCAR), missing at random (MAR), missing not at random (MNAR). In some examples, the process of replacing or imputing characteristics at Block 312 can be performed based on at least one selected from mean, zero, mode imputation; zero-order hold or last seen value; splines-based interpolation; assignment of a NaN or missingness indicator; multiple imputation (e.g., using chained equations); expectation maximization-based imputation; k-nearest neighbor-based imputation; and/or SVD-based and other factorization-based imputation.

In some examples, the process of augmenting the characteristics in at Block 314 can be performed by computing, for example but not limited to, summary statistics, such as a standard deviation, an average (e.g., an average cost over a time period), a trend (e.g., the slope of costs over time), distribution (e.g., a distribution of costs), histogram, count of one or more characteristics over one or more service records, etc. For example, repeated measurements of lab values such as cholesterol or other metabolic values can be summarized readily through these statistics.

The process of augmenting the characteristics can also be performed by computing values derived from rules and algorithms, such as whether a predefined threshold or other criterion is met or not (e.g., whether a provider should be labeled as fraudulent based on thresholds and/or criteria), as well as the assignment of values by logical rules, derived from one or more characteristics over one or more service records etc. For example, a blood pressure measurement above 120 mmHg may be augmented as 'High'.

The process of augmenting the characteristics can also be performed by a combination of one or more characteristics over one or more service records with other sources, such as might be obtained by enrichment with knowledge graphs for coded data (e.g., procedure, diagnostic, type and place of service, revenue etc. codes), treatments (e.g., drugs, procedures, monitoring, etc.), geography, providers, insurance plans and benefits etc. For example, zip codes may be used to derive higher-level features that are a reflection of the patients' environmental factors such as proximity to urgent/emergent care centers.

The process of augmenting the characteristics can also be performed by computing values derived from models, such as assignments to clusters, graphical model states, classifications, predictions, regression outputs, derived from one or more characteristics over one or more service records etc. For example, a risk score for future risk of hospital admission obtained from a model applied to a patient's characteristics. As another example, characteristics data can be inputted into a machine-learning model to identify clusters (e.g., various costs can be inputted into the model to identify clusters such as a high-cost cluster and a low-cost cluster) and the cluster identities can be assigned to the characteristics data (e.g., a particular cost can be assigned to belong to the high-cost cluster or the low-cost cluster). As another example, characteristics data can be inputted into a trained classification model and the output of the classification model can be used to augment the data (e.g., data of a particular patient can be inputted into a model that classifies the patient as high-risk or low-risk). As another example, characteristics data can be inputted into a prediction model and the output of the prediction model can be used to augment the data (e.g., data of a particular patient can be inputted into a model that outputs a risk of infection).

The process of augmenting the characteristics can also be performed by computing values derived from dimensionality reduction, such as autoencoding, embedding, factorization, multidimensional scaling, principal components analysis derived from one or more characteristics over one or more service records etc. For example, image data can be inputted into a contrastive model to obtain an embedding, which is a low-dimensional representation of the image. For example, a dimensionality reduced representation of a patient's features through Principal Component Analysis (PCA). The process of augmenting the characteristics can also be performed by computing values representing a distance or dissimilarity between one or more characteristics over one or more service records etc. For example, customized distance metrics may be defined to calculate the differences in a patient's physiological state.

At Block 120, the system can train one or more machine-learning models to predict one or more risk values and/or one or more risk trajectories in the absence of non-emergent care. In some embodiments, the system trains one or more models to predict the future risk if non-emergency care is not delivered over one or more predetermined time periods (e.g., 3 months, 6 months, 1 year, 3 years, 5 years, etc.) or over an indefinite period (when learning a function to predict outcomes over time) based on the data obtained through Blocks 110 and 114. These models can then be applied to one or more new members who are to be prioritized in the Block 140.

Figure 4A:
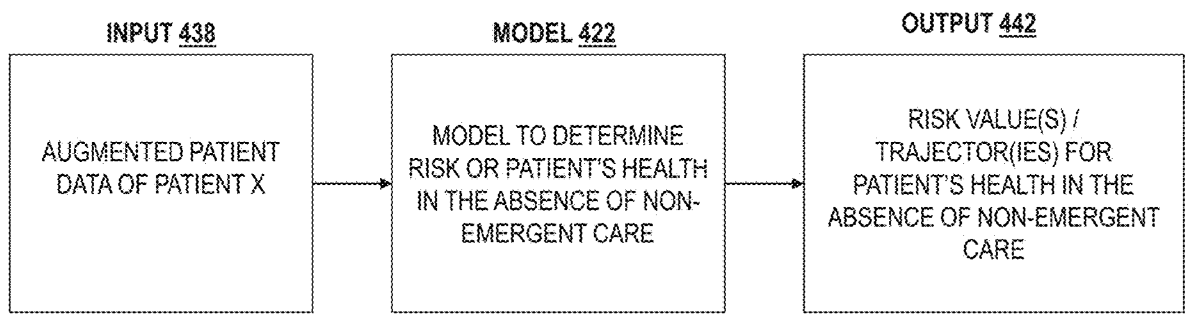
FIG. 4A illustrates an exemplary process for making a prediction using a machine-learning model, in accordance with some embodiments of this disclosure.

An exemplary model according to embodiments of this disclosure may be a trained deep neural network configured to receive as input features based on the augmented characteristics of patients and cases over a past period and output a risk value (e.g., hazard rate corresponding to the probability of an outcome as a function of time). For example, FIG. 4A illustrates a process of predicting one or more risk values and/or risk trajectories using model 422, e.g., model 122, according to embodiments of the present disclosure. As shown in the figure, augmented patient data 438 of a particular patient X can be input into a model 422. The model 422 can correspond to a prediction model to predict one or more risk values and/or risk trajectories for patient X in the absence of non-emergent care. The model 422 can then output 442 one or more predicted risk values and/or risk trajectories for patient X's health in the absence of non-emergent care.

In some examples, the model 422 can output multiple risk values corresponding to multiple risk metrics. In some examples, the risk values can include a predicted probability of an outcome within a timeframe, a predicted number of events of the outcome within a timeframe, a predicted time to the earliest occurrence of an event, etc. In some examples, each of the one or more risk values corresponds to a single point in time, e.g., a specific future time point. For example, a risk value can correspond to a predicted probability of an outcome in one month.

In some examples, each of the one or more risk trajectories corresponds to a time series of risk values. For example, a risk trajectory can correspond to the predicted probabilities of an outcome monthly over the next 6 months.

In some examples, the system can select a model based on whether the patient data includes an event. In some examples, the event may be a fiducial event or fiducial time point as discussed in greater detail below with respect to FIG. 4C. In some examples, the event can include, but is not limited to, a referral for a procedure or a visit, the last procedure or visit in a sequence of procedures or visits that the patient is undergoing, or the beginning of a seasonal allergy, medical condition, pandemic, natural disaster, etc. In some examples, the model 422 can be configured to predict risks for a patient when the specific event has occurred to the patient, e.g., the patient has received a referral for a specific procedure or type of care. In some examples, the model 422 can be configured to predict risks for a patient when the event has not occurred to the patient, e.g., the patient has not received a referral for a specific procedure or type of care. In this manner, the system can select an appropriate model based on whether the patient data indicates whether an event has occurred and which event has occurred.

Figure 4B:
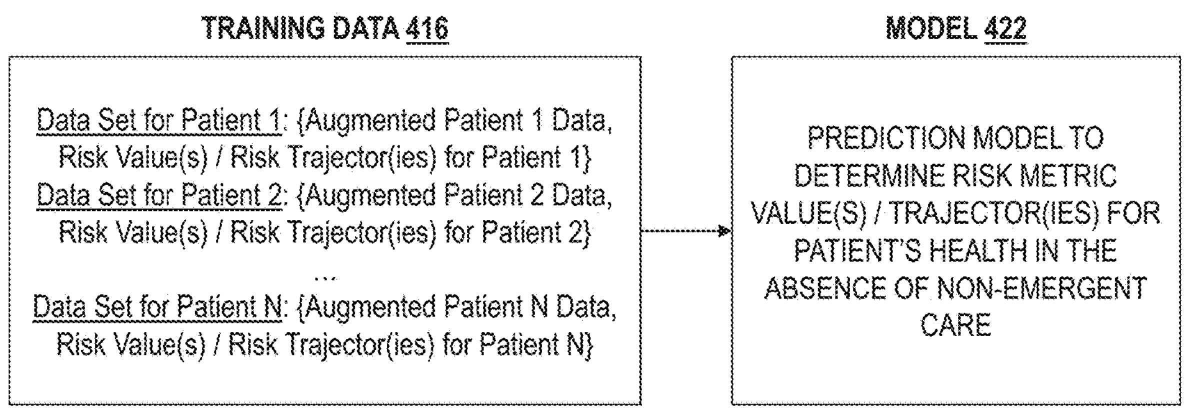
FIG. 4B illustrates an exemplary process for training a machine-learning model, in accordance with some embodiments of this disclosure.

FIG. 4B illustrates training at Block 120 according to embodiments of this disclosure. For example, the training at Block 120 can correspond to training model 422 described with respect to FIG. 4A. As shown in FIG. 4B, the training data 416 can be input into a model 422. The training data can include one or more data sets. As shown in the figure, each data set can include one or more inputs (e.g., augmented patient data) and one or more outcomes (e.g., a fiducial event) corresponding to a particular patient. In some embodiments, the model 422 can be trained to predict a set of one or more risk values and/or risk trajectories for a patient's health in the absence of non-emergent care. For example, model 422 can receive a data set for Patient 1 including augmented Patient 1 data and one or more actual risk values/trajectories for Patient 1. The model 422 can use the augmented patient data to predict one or more risk metric values/trajectories for the health of Patient 1 in the absence of non-emergent care. The predicted risk values/trajectories can be compared to the actual risk values/trajectories determined for Patient 1 to evaluate the accuracy of the model 422 and the model can be updated accordingly.

For example, without loss of generality, the exemplary model can be trained using data collected between the years 2015 and 2020, from 100,000 patients diagnosed with coronary artery disease and with information about which of these patients had a heart surgery, when the heart surgery happened, when the patients had heart attacks, and when the patients had other events (such as no longer being enrolled with the health plan or health system providing the data) that might have led to them being 'censored' in the data.

The exemplary model is trained in this setting to use the data from the 100,000 patients comprising augmented characteristics prior to the diagnosis of coronary artery disease to output a risk value for these patients comprising having heart attacks prior to the composite of heart surgery and/or censoring. Once this exemplary model is trained, it can be applied to new patients in 2021, by using feature vectors comprising the augmented characteristics of new patients diagnosed with coronary artery disease to predict the future risk values for these individuals (i.e., the probability of a heart attack as a function of time). While the example here is presented in the setting of a single outcome (heart attack), it can be readily extended to multiple outcomes (e.g., heart attack, stroke, seizure), e.g., by predicting multiple risk values and/or the risk values for composite outcomes. Similarly, while the example here is presented in the setting of a single procedure (e.g., heart surgery) it can be readily extended to multiple procedures (e.g., coronary angiography and heart surgery), e.g., by combining these procedures into a composite procedure and/or taking the first/last of these procedures as the procedure.

In various embodiments, the techniques of the present disclosure can be applied both to data where there is an initial fiducial time-point and where there is not. FIG. 4C illustrates exemplary training data 416C when there is an initial fiducial time-point and/or fiducial event, according to embodiments of this disclosure. FIG. 4D illustrates exemplary training data 416D when there is not an initial fiducial time-point, according to embodiments of this disclosure. The presence of an initial fiducial time-point can occur, for example, when there is a known event that triggers the subsequent non-emergent care being prioritized. For example, a fiducial time-point can include, but is not be limited to, a referral for a procedure or a visit, the last procedure or visit in a sequence of procedures or visits that the patient is undergoing, or the beginning of a seasonal allergy, pandemic, natural disaster, etc.

FIG. 4C illustrates exemplary training data 416C when there is an initial fiducial time-point, according to embodiments of this disclosure. For example, a model, e.g., model 422 can be trained using patient data corresponding to patients who receive non-emergent care of interest. Accordingly, models trained using data with one or more fiducial time-points can be configured to receive patient data with one or more fiducial time points. As shown in the figure, training data 416C can include: (i) patient characteristics and case characteristics corresponding to the history of each patient up to and including the fiducial time-point as features/inputs to the modeling; (ii) the outcomes occurring during the period between the fiducial time-point and the delivery of subsequent non-emergent care; (iii) the delay between the fiducial time-point and the delivery of subsequent non-emergent care; and (iv) actual risk values. In some examples, the actual risk values can be determined based on items (i)-(iii).

For example, for patients diagnosed with coronary artery disease and referred for a coronary angiography, the training data can include (i) patient characteristics at and up to the time of diagnosis and referral, (ii) the outcomes of heart attacks due to coronary artery disease prior to coronary angiography, and (iii) delays between the point of diagnosis and referral and the subsequent performance of coronary angiography. The actual risk values can be (iv) the number of heart attacks the patient experienced, whether the patient has developed complications, etc. The model 422 can use the training data 416C to predict a set of risk values for the health of a corresponding patient in the absence of non-emergent care. The set of one or more risk values determined by model 422 for a patient, e.g., patient 1, can be compared to (iv) the actual risk values for the respective patient, to evaluate the accuracy of the model 422 (e.g., to calculate a loss) and train the model (e.g., based on the calculated loss).

FIG. 4D illustrates exemplary training data 416D when there is not an initial fiducial time-point, according to embodiments of this disclosure. In such embodiments where there is an absence of an initial fiducial time-point, repeated data sets can be created for patients who receive the non-emergent care of interest across multiple calendar time-points. Accordingly, models trained using data without a fiducial time-point can be configured to receive patient data without a fiducial time point. For example, training data 416D can include (i) patient characteristics and case characteristics corresponding to the history of each patient up to and including the calendar time-point as features/inputs to the modeling, (ii) the outcomes occurring during the period between the calendar time-point and the delivery of subsequent non-emergent care, and (iii) the delay between the calendar time-point and the delivery of subsequent non-emergent care; and (iv) actual risk values. In some examples, the estimated risk values can be determined based on items (i)-(iii).

These datasets can be repeated across multiple time-points (e.g., with a monthly, quarterly, semi-annual, annual etc. lag). In each case, considering patients who go on to receive the non-emergent care of interest within a given timeframe following each time-point. For example, data from multiple years (e.g., 2015 to 2020) can be used for modeling patients diagnosed with coronary artery disease and referred for a coronary angiography. In such examples, the training data 416D can include: (i) the patient characteristics between the period of Jan. 1, 2015 to Dec. 31, 2019, (ii) the outcome of heart attacks due to coronary artery disease prior to coronary angiography during the same time period, and (iii) the delay between Jan. 1, 2020 and the subsequent performance of coronary angiography. The model 422 can use the training data 416D to predict a set of risk values for the health of a corresponding patient in the absence of non-emergent care. The set of one or more risk values determined by model 422 for a patient, e.g., patient 1, can be compared to (iv) the actual risk values for the respective patient, to evaluate the accuracy of the model 422.

In some embodiments, the techniques of the present disclosure can be applied both to data where patients eventually received the non-emergent care (i.e., labelled examples) or did not (i.e., censored examples). In embodiments where a patient did not receive non-emergent care after an initial fiducial time-point, the time period between this fiducial time point and the last known follow up for the patient (and all associated outcomes during this time period) can be used to augment the modeling process with partially labeled (i.e., censored) examples.

In some embodiments, the model training can be accomplished through the use of binary or multi-class classification to predict each outcome (including logistic regression, support vector, decision tree/random forest, neural network and deep learning, nearest neighbor-based classification etc.), the use of regression to predict the number of events for each outcome or the time to the earliest event for each outcome using linear or polynomial regression (including LASSO, ridge, elastic net, robust, hierarchical approaches etc.) or other regression approaches (including support vector, decision tree/random forest, neural network and deep learning, nearest neighbor-based regression etc.). Such embodiments may be limited in its ability to account for the variable amounts of time each patient has outcome observed data for prior to their non-emergent care being delivered, as well as its ability to account for patients that did not receive non-emergent care in the observable timeframe.

In some embodiments, the model training may be accomplished through the following methods: Cox and adaptive LASSO proportional hazards regression, survival trees and forests, support vector machines for censored data, deep-learning based approaches for censored data, or a combination thereof. Such embodiments may be able to account for the variable amounts of time each patient has outcome observed data for prior to their non-emergent care being delivered, as well as account for patients that did not receive non-emergent care in the observable timeframe.

In one or more embodiments, the predicted risk for each outcome can include: the predicted probability of an outcome within a timeframe, the predicted number of events of the outcome within a timeframe, the predicted time to the earliest occurrence of an event of the outcome, the predicted time-series of outcome events as a function of time, the predicted time-series of outcome probabilities as a function of time, the predicted relative risk of patients with respect to each other, or a combination thereof.

In some embodiments, the model can output the impact of patient characteristics on an estimated baseline risk metric. In such examples, the impact of patient characteristics on a baseline risk metric can be determined, e.g., an increase or decrease of a patient's risk metric based on patient characteristics found in the patient data. Examples according to this embodiment can be implemented by using one or more internal and holdout layers followed by an output node. In some examples, the output node can include a linear activation that estimates the log-risk Cox function.

Figure 5A:
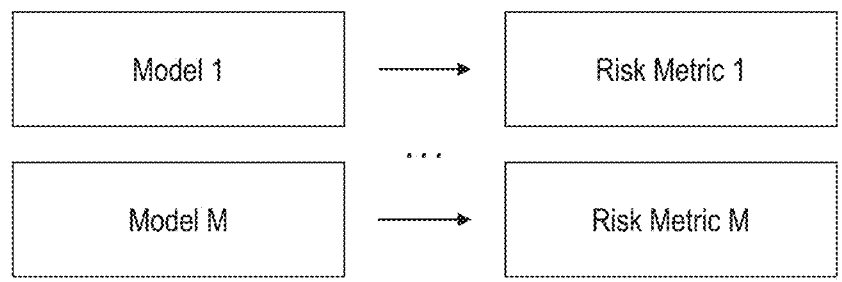
FIGS. 5A-5C illustrate exemplary machine-learning models, in accordance with some embodiments of this disclosure.
Figure 5B:
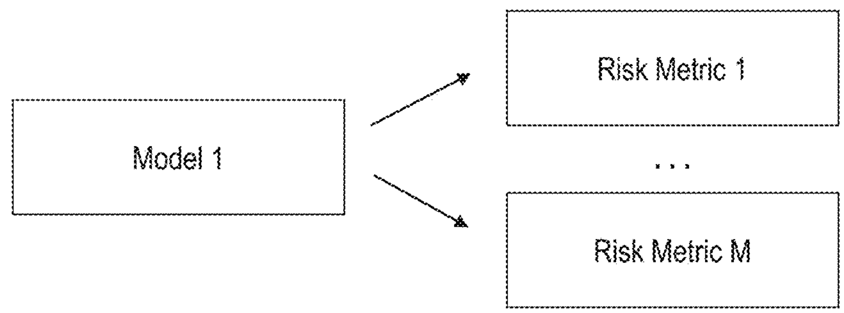
Figure 5C:
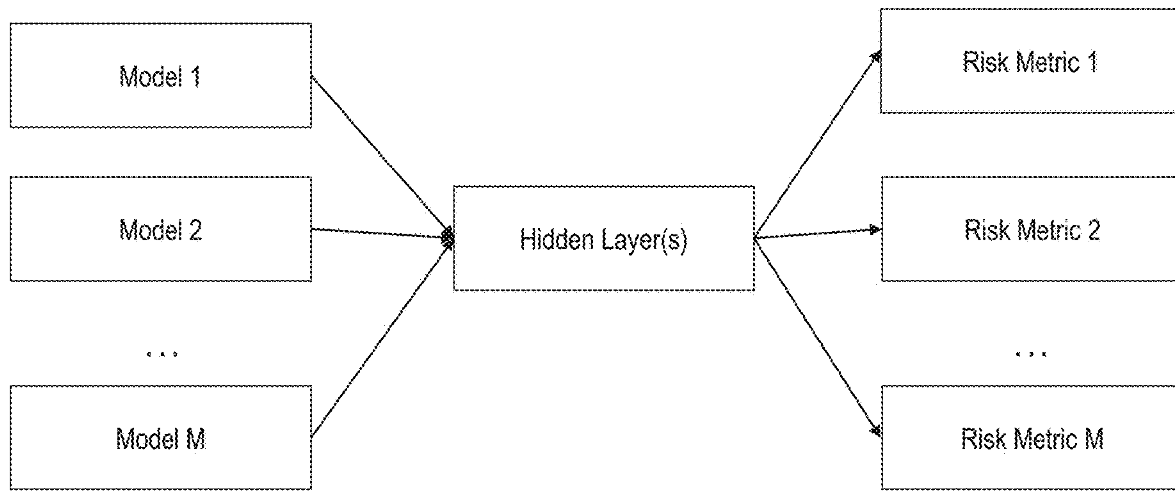

FIGS. 5A-5C illustrate exemplary machine-learning models and outputs, according to embodiments of the present disclosure. In some embodiments, a single model may be used to predict a single outcome, e.g., for X outcomes there may be X models that are separately trained to each predict one outcome. For example, as shown in FIG. 5A. Model 1 can generate a risk value corresponding to Risk Metric 1, while Model M can generate a risk value corresponding to Risk Metric M. In some examples, each risk metric can be associated with one or more health conditions. In some embodiments, a single model may be used to predict one or more outcomes, e.g., for X outcomes there may be one model that predicts X outcomes. For example, as shown in FIG. 5B, Model 1 can generate risk values corresponding to Risk Metric 1-M. In some examples, each risk metric can be associated with one or more health conditions.

In some embodiments, a single model can be jointly trained with one or more models, where each model can predict a single outcome (i.e., for X outcomes we have X models that are jointly trained to each predict one outcome). For example, as shown in FIG. 5C, Model 1, Model 2, and Model M are configured to generate Risk Metrics 1-M that can share structures (e.g., hidden layers). In some examples, each risk metric can be associated with one or more health conditions. In such embodiments, sharing a structure can include, but not be limited to: multi-task learning (including task coupled parameter formulation, co-training, mean regularization, joint feature selection, alternating structural optimization, low rank and sparse learning, clustering learning, and the use of graph structures to achieve multi-task learning) and transfer learning and domain adaptation.

The various embodiments above can be used individually or in conjunction with each other.

At Block 130, the system retrieves data for new patient(s) that may require prioritization. In some embodiments, the system receives one or more identifiers for new patients requiring prioritization (through one or more of an API call with identifiers, a file transfer with identifiers, a web request or other input from a connected application etc.). In what follows, both in this section and in ensuing sections, the sequence of steps needed for a single new patient is described. A skilled artisan will understand that these steps are readily extendable to the scenario where more than one patient needs to be prioritized.

In some embodiments, the system retrieves (from a database of historical records) the patient data 132 for a potential individual to be prioritized for non-emergent care. In some examples, patient data 132 can correspond to one or more patients. In some examples, the patient data 132 can include, but not limited to, characteristics of the patient and past care service records for the patient. In some examples, patient characteristics can include, but not be limited to, e.g., demographic information such as age and sex; acute and chronic health history; history and physical exam findings; past medical, surgical and prescription history; family history; occupational history; social history; review of systems; social determinants of health etc., across multiple years 1-Y. In some examples, past care service records for the patient can include, but not be limited to, e.g., professional, facility and pharmacy claims; electronic health records; self-reported outcomes; digital health records; social media records; data from labs, assays, and other tests; etc.) across multiple years 1-Y.

Figure 6:
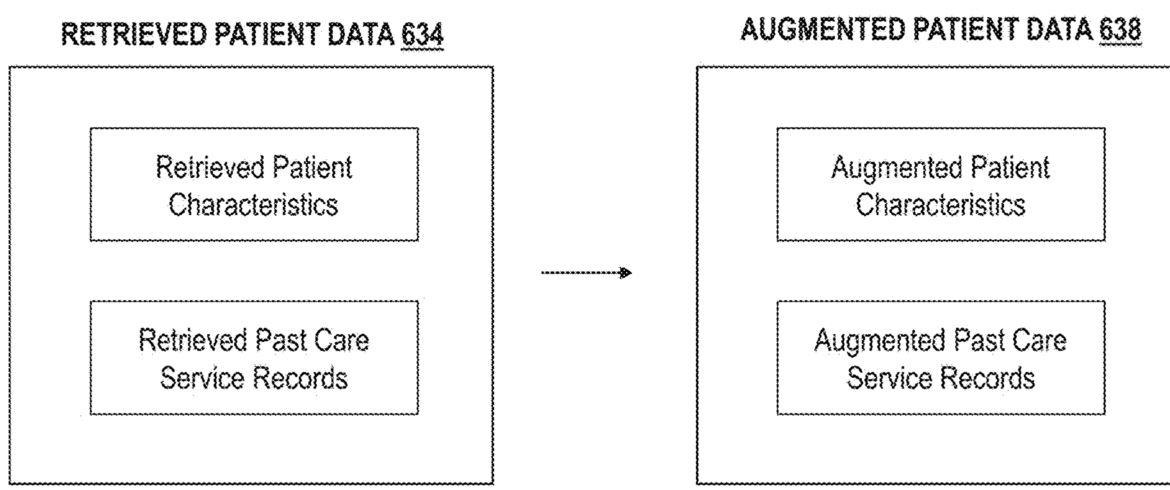
FIG. 6 illustrates an exemplary process for determining prioritization of care services provided to a patient, in accordance with some embodiments of this disclosure.

At Block 136, the system can augment data for new patient(s) requiring prioritization for non-emergent care and/or services. FIG. 6 illustrates patient data augmentation 636, e.g., corresponding to Block 136. For example, the retrieved patient data 634 corresponding to retrieved patient characteristics and retrieved past care service records can be augmented to obtain augmented patient data 638 that include augmented patient characteristics and augmented past care service records. In one or more examples, the system can augment the data for the new patient in a manner similar to the augmentation of the data for patients as described in Block 114. For example, the system can augment the patient data 634 (e.g., data retrieved in Block 130) by either replacing or imputing characteristics that were otherwise attempted to be retrieved for providers, patients and cases, but were missing or found to be noisy or augmenting the characteristics retrieved for providers, patients and cases with additional attributes.

Figure 7:
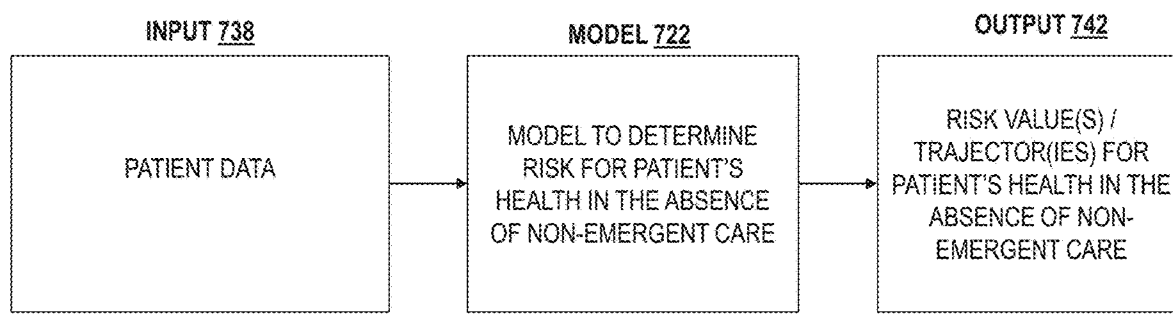
FIG. 7 illustrates an exemplary process for determining a risk value associated with a patient, in accordance with some embodiments of this disclosure.

At Block 140, the system can predict risk values 142 for new patients in the absence of non-emergent care. In some embodiments, the system predicts the risk trajectories 142, e.g., time-varying risks of future outcomes, for the new patient using the models trained at Block 120. FIG. 7 illustrates predicting one or more risk values or risk trajectories in the absence of non-emergent care at Block 150, according to embodiments of this disclosure. As shown in the figure, patient data 738 can be input into model 722, e.g., corresponding to model 122 to predict one or more risk values for a patient's health in the absence of non-emergent care. In some examples, the patient data as input to the models 122 can be derived from the augmented data 138 obtained at Blocks 130 and 136 using the same process as in Block 114 to derive the features from the augmented patient data 112 obtained through Blocks 110 and 114.

In various embodiments, the predictions can include: the predicted probability of an outcome within a timeframe, the predicted number of events of the outcome within a timeframe, the predicted time to the earliest occurrence of an event of the outcome, the predicted time-series of outcome events as a function of time, the predicted time-series of outcome probabilities as a function of time, the predicted relative risk of patients with respect to each other, or a combination thereof.

In some embodiments, the system can select the model based on the patient data 738. For example, if the patient data 738 includes one or more fiducial events, the system can select a corresponding model that was trained using training data that included fiducial events, e.g., trained with training data 416C. If the patient data 738 does not include one or fiducial events, the system can select a corresponding model that was trained using training data without fiducial events, e.g., trained with training data 416D.

In some embodiments, the patient data can 738 be input into one or more different models. For example, referring briefly to FIG. 5A, the patient data 738 can be input into Model 1 through Model N to predict Risk Metric 1 through Risk Metric N, respectively. In some examples, the system can select a model corresponding to a risk metric of interest. For example, if the objective of the system is to predict a risk metric associated with a heart condition of a patient, the system can select a model that will provide the risk metric of interest relevant to the heart condition of the patient. For example, if the Risk Metric 1 is associated with seizures, while Risk Metric M is associated with a heart condition, the system can input data into Model M and forgo inputting data into Model 1 to receive one or more risk values relevant to the heart condition. As another example, referring briefly to FIG. 5C, the patient data 738 can be input into Model 1 through Model N to jointly predict Risk Metric 1 through Risk Metric N, respectively. In some embodiments, the patient data 738 can be input into a single model. For example, the patient data 738 can be input into Model 1 of FIG. 5B.

Figure 8:
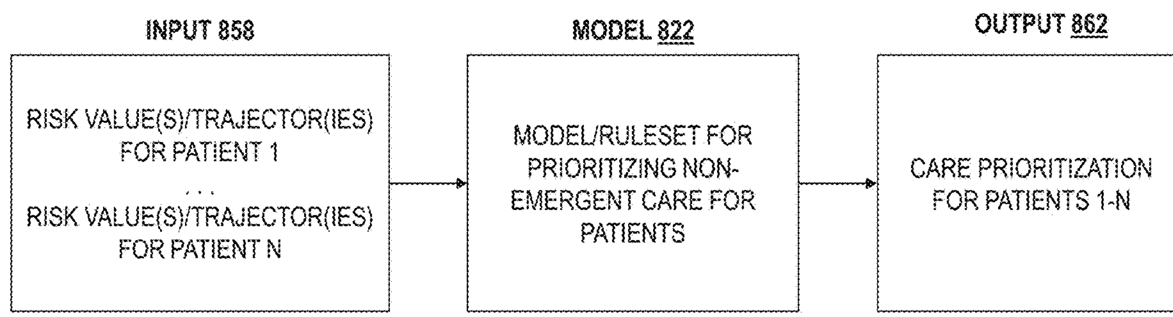
FIG. 8 illustrates an exemplary process for determining prioritization of care services provided to a patient, in accordance with some embodiments of this disclosure.

At Block 150, the system can use the predicted risk trajectories 142 to prioritize the delivery of non-emergent care. In some examples, the system can prioritize the non-emergent care for one or more patients. In some examples, a model and/or ruleset may be used to prioritize non-emergent care for one or more patients. FIG. 8 illustrates prioritizing non-emergent care for a patient, according to embodiments of this disclosure. As shown in the figure, the input 858 for the model 822 can include one or more risk values and/or risk trajectories corresponding to a set of one or more patients (e.g., patients 1-N). In some examples, risk values for one or more types of care services and/or health events can be input into the model 822. In some examples, the input 858 can include risk values and/or trajectories from one or more models. For example, the input 858 can include risk values from one or more models that were trained using training data 416C, e.g., training data that included fiducial events, and one or more models that were trained using training data 416D, e.g., training data that did not include fiducial events. In some examples, the model 822 can compare the one or more risk values and output a care prioritization 862 corresponding to one or more patients. For example, the model 822 can indicate a relative priority of one or more patients. In some examples, the model 822 can compare the one or more risk values and output a care prioritization 862 corresponding to one or more types of care for a single patient. For example, the model 822 can indicate a relative priority of one or more types of non-emergent care to be provided to the patient.

With a knowledge of the anticipated needs of care services of one or more patients and the prioritization of these anticipated needs, the system triggers or causes, manually or automatically, action to be taken by health plans and provider systems of the next steps post prioritization. This action can be implemented via a multi-modal approach to ensure that the prioritization recommendation is presented to the decision maker, e.g., provider, at the point of decision in real-time.

In some embodiments, the outputs of the models can be used in a direct to health plan and provider mode to act on the prioritization recommendation by setting up the next steps (laboratory test, telemedicine visits, in person visits, specialist appointments and procedure scheduling. In this mode, the action is part of health plan care manager facing applications or provider system (provider and care team) facing applications (websites, mobile applications, call centers) that health plans and provider organization may use to manage, prioritize, schedule and communicate with patients and inform them of information related to their health care including care prioritization.

In some embodiments, the outputs of the models and the recommendation of prioritization across multiple patients, potentially segmented by need of similar specialists or procedures, can be provided to health plans and provider systems at a timed cadence (daily, weekly, monthly etc.) to highlight high priority patients for the health plans and provider systems to manage and schedule proactively.

In some embodiments, the system serves up prioritization recommendations directly to providers or care team members who are working to select further care and evaluation of a patient. In this mode, the recommendation is available to the health plan care manager via deep integration to the health plan's care management portal or application and it is available to the provider and provider care teams via deep integration with the provider's Electronic Health Record (EHR) application. The EHR facing integration is part of the provider workflow that allows seamless integration and use by simple clicks and drop down menus to receive prioritization recommendations in real-time for immediate action. This real-time action will result in specific next steps in the care journey of specific patients including but not limited to a next appointment with a specialist, an appointment for a procedure, laboratory test, alternate care path when deemed necessary etc.

In an exemplary embodiment, the output can be compared to a predefined threshold. If the threshold is exceeded (e.g., patient risk of an adverse outcome within the next month is greater than 10%) the system can automatically schedule the patient for a care service. For example, the system can make an API call or conduct an electronic transaction within a scheduling system and inform. The system can further send a notification to the patient about the scheduled care service via e-mail, text, or in-app notification.

In some embodiments, if the threshold is exceeded (e.g., patient risk of an adverse outcome within the next month is greater than 10%) the system can automatically alert care providers, advocates and/or managers through e-mail, text, pager, or in-app notification. In some embodiments, the comparison can be used to sort patients based on which patients are at greatest risk of near term outcomes. For example, the top ranked patient may correspond to the patient with the highest risk within the next month, the second ranked patient may correspond to the patient with the second highest risk within the next month, and so on. The ranked list can be electronically transmitted to providers, advocates and care managers with directions to work through the list in a sorted manner from highest risk to lowest risk and target care pathways to each patient to reduce risk.

Figure 9A:
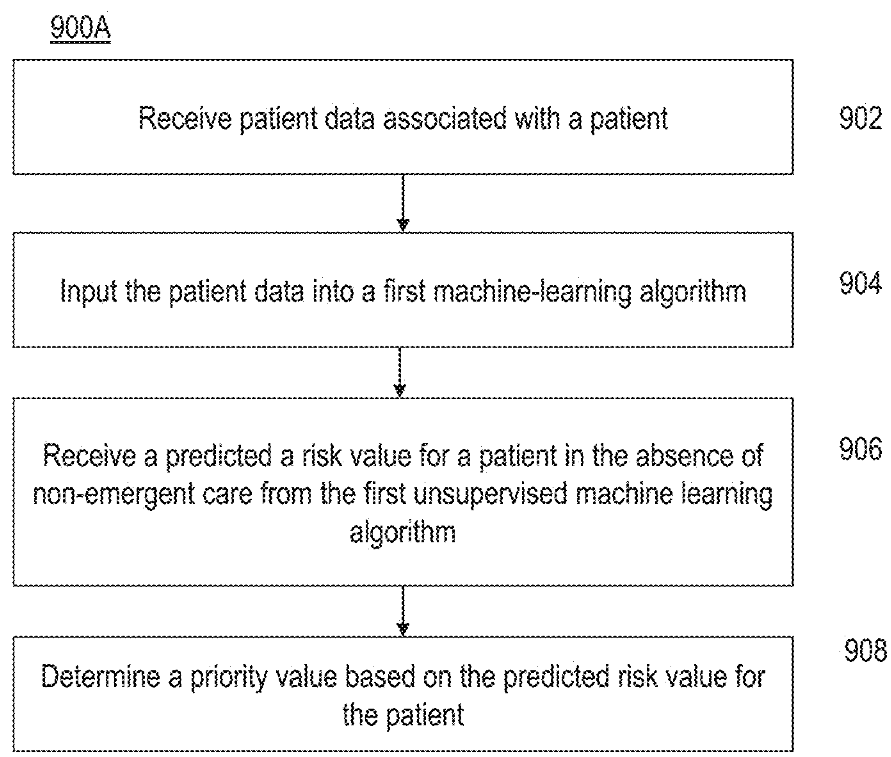
FIGS. 9A-9B illustrate an exemplary process for determining prioritization of care services provided to a patient, in accordance with some embodiments of this disclosure.

FIG. 9A illustrates a flow chart of a process 900 for determining a prioritization of care for a patient, according to embodiments of the present disclosure. In some embodiments process 900 can correspond to one or more blocks of process 100. At Block 902, the system can receive patient data associated with a patient. In some examples, the patient data can correspond to a first time period. In some embodiments, Block 902 can correspond to Block 142 described above. At Block 904, the system can input the patient data into a first machine-learning algorithm. At Block 906, the system can receive a predicted a risk value for a patient in the absence of non-emergent care from the first machine learning algorithm. In some embodiments, Block 906 can correspond to Block 150. At Block 908, the system can determine a priority, e.g., a priority value, based on the predicted risk value for the patient. For example, the priority value can correspond to the priority of a patient receiving a particular type of care service relative to one or more other patients and/or relative to one or more types of care services. In some examples, Block 908 can correspond to Block 160.

Figure 9B:
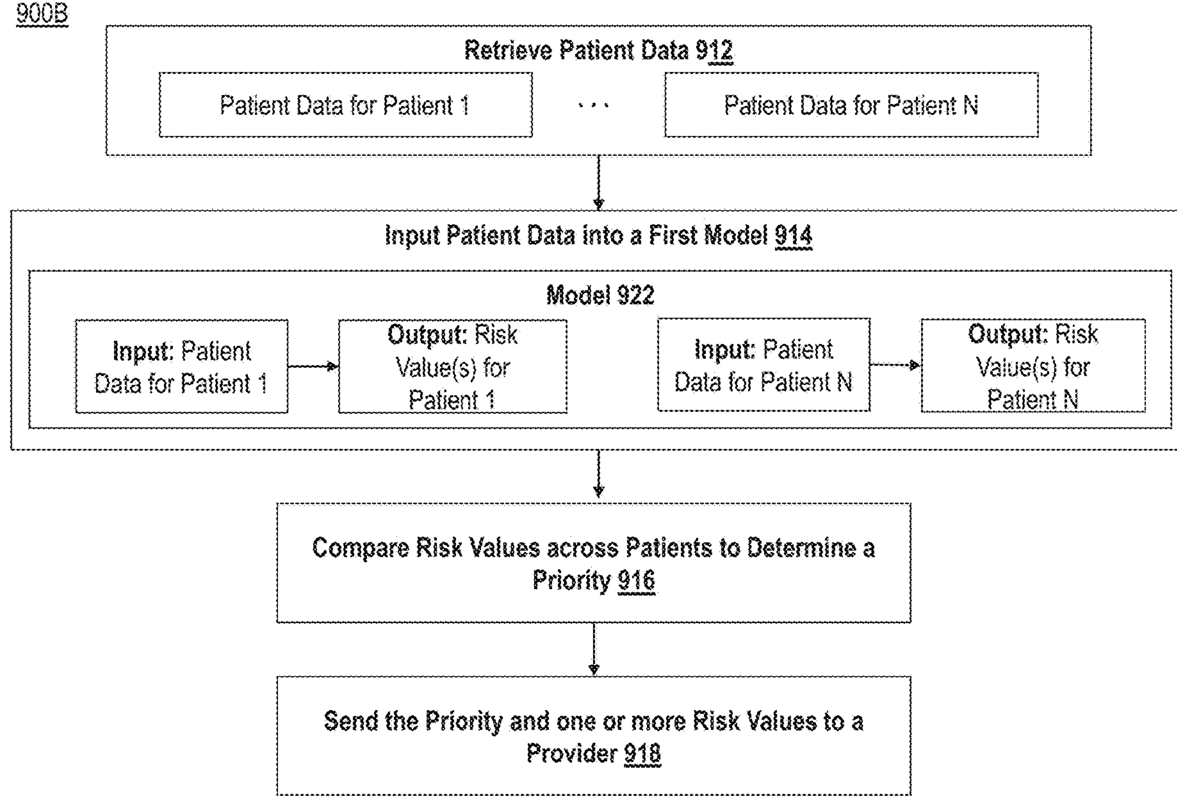

FIG. 9B illustrates a flow chart of a process 900B for determining a prioritization of care for a patient, according to embodiments of the present disclosure. At Block 912, the system can retrieve patient data. As shown in the figure, the system can retrieve patient data for one or more patients, e.g., Patient 1-N. In some embodiments, Block 912 can correspond to Block 130. At Block 914, the system can input patient data into a first machine-learning model. As shown in the figure, the machine-learning model 922 can receive inputs corresponding to datasets for a plurality of patients, e.g., Patients 1-N. The model can be configured to output a predicted risk value for a corresponding patient. In some examples, model 922 can correspond to model 122, model 422, and/or model 722 described above. In some examples, Block 914 can correspond to Block 140 described above.

At Block 916, the system can compare the risk values across the one or more patients to determine a prioritization for the distribution of non-emergent care to the one or more patients. In some embodiments, the prioritization can correspond to a single patient. In some embodiments, the prioritization can correspond to one or more patients, e.g., one or more priority values can be generated for each patient indicative of a prioritization of the respective patient. In some examples, Block 916 can be performed by a model or ruleset, e.g., model 822.

In some examples, the system can aggregate the one or more risk values for each patient to determine a prioritization of the patients. For example, the system can take an average of the risk values for each patient to determine the prioritization.

In some examples, the system can determine the prioritization based on one or more metrics of interest corresponding to the predicted risk metrics. In some embodiments, the metric of interest may vary depending on a type of provider. For example, the one or more metrics of interest relevant to an emergency room (ER) department may differ from the one or more metrics of interest to a cardiology department. In some examples, the system can select the one or more metrics of interest based on an association of the predicted risk metric with a particular health condition. For example, the system may select one or more risk metrics associated with cardiac conditions and/or cardiovascular disease to be sent to a cardiology department. As another example, the system may consider one or more risk trajectories when prioritizing one or more patients for an ER department. For example, patient with a high risk trajectory, indicative of a quickly deteriorating condition, may be prioritized over a patient with a low risk trajectory, indicative of a relatively stable condition.

In some examples, the one or more risk values can be used to determine a prioritization of care for a single patient. For example, if a first set of one or more of the predicted risk values for a patient is associated with a first health condition, e.g., seizures, and a second set of one or more of the predicted risk values for the patient is associated with a second health condition, e.g., diabetes, then the system can prioritize care and/or treatment for these health conditions based on the one or more predicted risk values.

At Block 918, the system can send the prioritization and/or one or more of the risk values to a provider. For example, in some embodiments, the prioritization and the risk value corresponding to the highest priority patient can be sent to the provider. The provider and/or system can then schedule, manage, and/or provide care as discussed above.

Figure 10:
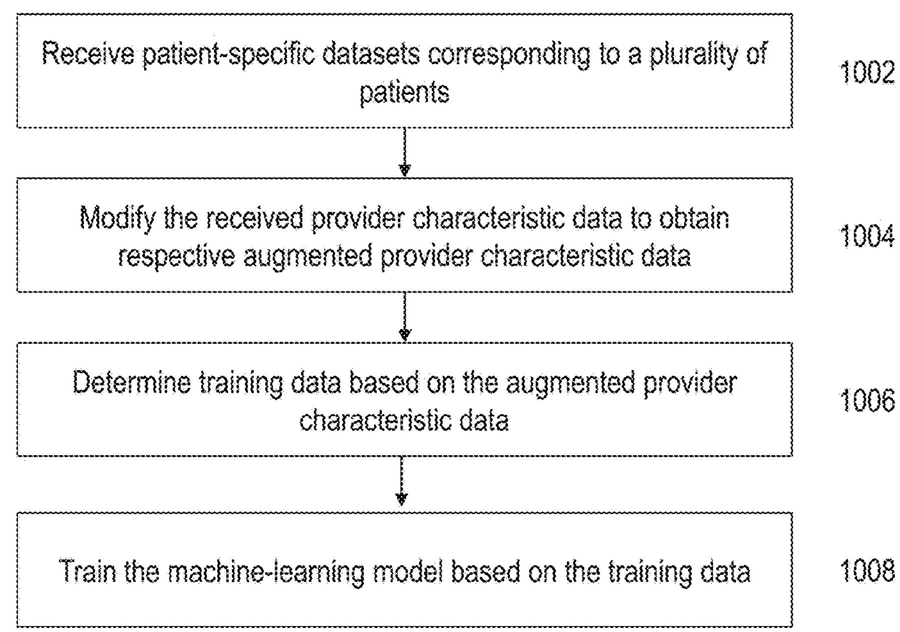
FIG. 10 illustrates an exemplary process for training a machine-learning model, in accordance with some embodiments of this disclosure.

FIG. 10 illustrates a flow chart of a process 1000 for training a machine-learning model according to embodiments of this disclosure. In some embodiments process 1000 can correspond to one or more blocks of process 100. At Block 1002, the system can receive patient-specific datasets corresponding to a plurality of patients. For example, the patient data can include patient characteristics and case history, as discussed above. In some examples, Block 1002 can correspond to Block 110 described above. At Block 1004, the system can modify the received patient data to obtain respective augmented patient data. In some examples, Block 1004 can correspond to Block 114 described above. At Block 1006, the system can determine training data based on the augmented patient data. In some examples, the training data can be determined as described above with respect to FIGS. 4B-4D. At Block 1008, the system can train the machine-learning model based on the training data. In some examples, Block 1008 can correspond to Block 120 described above.

Figure 11:
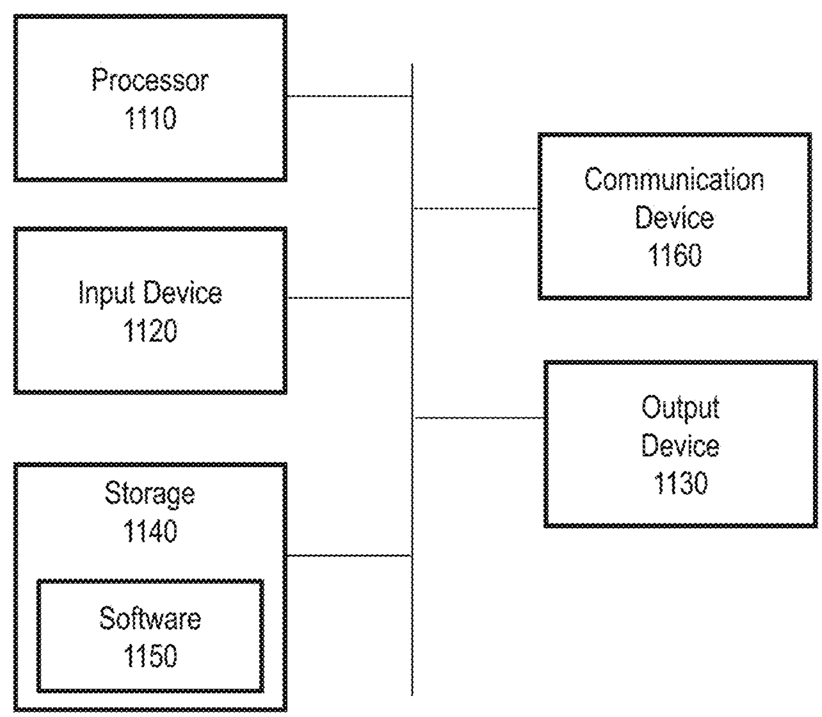
FIG. 11 illustrates an exemplary electronic device, in accordance with embodiments of this disclosure.

The operations described above with reference to FIGS. 1, 2A-2C, 3, 4A-4D, 5A-5C, and 6-10 are optionally implemented by components depicted in FIG. 11. It would be clear to a person having ordinary skill in the art how other processes are implemented based on the components depicted in FIG. 11.

FIG. 11 illustrates an example of a computing device in accordance with one embodiment. Device 1100 can be a host computer connected to a network. Device 1100 can be a client computer or a server. As shown in FIG. 11, device 1100 can be any suitable type of microprocessor-based device, such as a personal computer, workstation, server or handheld computing device (portable electronic device) such as a phone or tablet. The device can include, for example, one or more of processor 1110, input device 1120, output device 1130, storage 1140, and communication device 1160. Input device 1120 and output device 1130 can generally correspond to those described above, and can either be connectable or integrated with the computer.

Input device 1120 can be any suitable device that provides input, such as a touch screen, keyboard or keypad, mouse, or voice-recognition device. Output device 1130 can be any suitable device that provides output, such as a touch screen, haptics device, or speaker.

Storage 1140 can be any suitable device that provides storage, such as an electrical, magnetic or optical memory including a RAM, cache, hard drive, or removable storage disk. Communication device 1160 can include any suitable device capable of transmitting and receiving signals over a network, such as a network interface chip or device. The components of the computer can be connected in any suitable manner, such as via a physical bus or wirelessly.

Software 1150, which can be stored in storage 1140 and executed by processor 1110, can include, for example, the programming that embodies the functionality of the present disclosure (e.g., as embodied in the devices as described above).

Software 1150 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1140, that can contain or store programming for use by or in connection with an instruction execution system, apparatus, or device.

Software 1150 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 1100 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1100 can implement any operating system suitable for operating on the network. Software 1150 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

The invention claimed is:

1. A computer-implemented method for using machine-learning to generate a medical recommendation, comprising:

receiving, by one or more processors, historical patient data and one or more historical risk values associated with a plurality of patients;

modifying, by the one or more processors, the historical patient data by:

computing one or more characteristics missing from the historical patient data, and adding the computed one or more characteristics to the historical patient data to obtain augmented historical patient data;

training a machine-learning model by:

inputting the augmented historical patient data into the machine-learning model to obtain one or more estimated risk values, and updating the machine-learning model based on a comparison of the one or more estimated risk values to the one or more historical risk values;

receiving, by the one or more processors, first patient data associated with a first patient;

modifying, by the one or more processors, the retrieved first patient data by:

computing a first set of characteristics missing from the retrieved first patient data, and adding the computed first set of characteristics to the retrieved first patient data to obtain augmented first patient data;

receiving, by the one or more processors, second patient data associated with a second patient;

modifying, by the one or more processors, the retrieved second patient data by:

computing a second set of characteristics missing form the retrieved second patient data, and adding the computed second set of characteristics to the retrieved second patient data to obtain augmented second patient data;

inputting the augmented first patient data into the trained machine-learning model to determine a first set of one or more risk values for the first patient;

inputting the augmented second patient data into the trained machine-learning model to determine a second set of one or more risk values for the second patient;

comparing the first set of one or more risk values and the second set of one or more risk values to determine a priority for distributing care to the first patient and the second patient; and in accordance with the determination that the first patient has priority, generating a medical recommendation based on the priority, wherein the medical recommendation comprises an identification of a treatment for the first patient.

2. The method of claim 1, wherein a risk value of the first set of one or more risk values corresponds to: a probability of an outcome within a time frame, a number of events of the outcome within a time frame, a time to a first occurrence of the outcome, a time-series of outcome events as a function of time, or the time-series of outcome probabilities as a function of time.

3. The method of claim 1, further comprising automatically scheduling an appointment for the first patient.

4. The method of claim 1, further comprising sending a notification to a provider, wherein the notification recommends distributing care to the first patient based on the priority.

5. The method of claim 1, further comprising displaying the medical recommendation to a provider.

6. The method of claim 1, further comprising sending a notification to the first patient, wherein the notification recommends next steps for distributing care to the first patient.

7. The method of claim 1, wherein generating the medical recommendation comprises identifying a first treatment for the first patient.

8. The method of claim 1, further comprising sending the second set of one or more risk values to a provider, wherein generating the medical recommendation comprises identifying a second treatment for the second patient based on the priority.

9. The method of claim 1, wherein electronic health records of the first patient are updated to include the priority and the first set of one or more risk values.

10. The method of claim 1, further comprising selecting the trained machine-learning model from a plurality of trained machine-learning models based on one or more events that have occurred to the first patient and the second patient.

11. The method of claim 1, further comprising determining an updated first set of one or more risk values and an updated second set of one or more risk values at regular intervals, and determining an updated priority based on the updated first set of one or more risk values and the updated second set of one or more risk values.

12. The method of claim 1, wherein the first patient data comprises patient characteristics, care service records, or a combination thereof.

13. The method of claim 12, wherein the patient characteristics comprise demographic information, acute and chronic health history, history and physical exam findings, medical history, surgical history, prescription history, family history, occupational history, social history, review of systems, social determinants of health, or a combination thereof.

14. The method of claim 12, wherein the care service records comprise a medical professional claim, a medical facility claim, a pharmacy claim, electronic health records, self-reported outcomes, digital health records, social media records, data from laboratory test, or a combination thereof.

15. The method of claim 1, wherein the trained machine-learning model is configured to receive a patient-specific dataset and output a third set of one or more risk values indicative of a health of a corresponding patient in the absence of care.

16. The method of claim 1, wherein the historical patient data comprises a plurality of patient-specific datasets for the plurality of patients, each patient-specific dataset comprising one or more of: patient characteristics at diagnosis, patient outcomes in the absence of non-emergent care, and delays between the diagnosis and receiving the non-emergent care.

17. The method of claim 1, wherein the historical patient data comprises one or more fiducial time points.

18. The method claim 1, further comprising modifying, by the one or more processors, the received patient data to obtain respective augmented patient data, and wherein inputting the patient data into the first trained machine-learning model comprises inputting the augmented patient data into the first trained machine-learning model.

19. The method of claim 1, wherein computing the first set of characteristics missing from the retrieved first patient data comprises computing one or more summary statistics.

20. The method of claim 1, wherein computing the first set of characteristics missing from the retrieved first patient data comprises determining whether a predefined threshold is met.

21. The method of claim 1, wherein computing the first set of characteristics missing from the retrieved first patient data comprises computing one or more values derived from a model.

22. The method of claim 21, wherein the model comprises one or more of: a dimensionality reduction model, a clustering model, a graphical model, a classifier, a prediction model, and a regression model.

23. The method of claim 1, wherein computing the first set of characteristics missing from the retrieved first patient data comprises retrieving one or more characteristics from a knowledge graph.

24. A system for generating a medical recommendation, comprising:

one or more processors;

a memory; and one or more programs, wherein the one or more programs are stored in the memory and configured to be executed by the one or more processors, the one or more programs including instructions for:

receiving, by one or more processors, historical patient data and one or more historical risk values associated with a plurality of patients;

modifying, by the one or more processors, the historical patient data by:

computing one or more characteristics missing from the historical patient data, and adding the computed one or more characteristics to the historical patient data to obtain augmented historical patient data;

training a machine-learning model by:

inputting the augmented historical patient data into the machine-learning model to obtain one or more estimated risk values, and updating the machine-learning model based on a comparison of the one or more estimated risk values to the one or more historical risk values;

receiving, by the one or more processors, first patient data associated with a first patient;

modifying, by the one or more processors, the retrieved first patient data by:

computing a first set of characteristics missing from the retrieved first patient data, and adding the computed first set of characteristics to the retrieved first patient data to obtain augmented first patient data;

receiving, by the one or more processors, second patient data associated with a second patient;

modifying, by the one or more processors, the retrieved second patient data by:

computing a second set of characteristics missing form the retrieved second patient data, and adding the computed second set of characteristics to the retrieved second patient data to obtain augmented second patient data;

inputting the augmented first patient data into the trained machine-learning model to determine a first set of one or more risk values for the first patient;

inputting the augmented second patient data into the trained machine-learning model to determine a second set of one or more risk values for the second patient;

comparing the first set of one or more risk values and the second set of one or more risk values to determine a priority for distributing care to the first patient and the second patient; and in accordance with the determination that the first patient has priority, generating a medical recommendation based on the priority, wherein the medical recommendation comprises an identification of a treatment for the first patient.

25. A non-transitory computer-readable storage medium storing one or more programs, the one or more programs comprising instructions, which when executed by one or more processors of one or more electronic devices, cause the electronic devices to:

receive, by one or more processors, historical patient data and one or more historical risk values associated with a plurality of patients;

modify, by the one or more processors, the historical patient data by:

computing one or more characteristics missing from the historical patient data, and adding the computed one or more characteristics to the historical patient data to obtain augmented historical patient data;

train a machine-learning model by:

inputting the augmented historical patient data into the machine-learning model to obtain one or more estimated risk values, and updating the machine-learning model based on a comparison of the one or more estimated risk values to the one or more historical risk values;

receive, by the one or more processors, first patient data associated with a first patient;

modify, by the one or more processors, the retrieved first patient data by:

computing a first set of characteristics missing from the retrieved first patient data, and adding the computed first set of characteristics to the retrieved first patient data to obtain augmented first patient data;

receive, by the one or more processors, second patient data associated with a second patient;

modify, by the one or more processors, the retrieved second patient data by:

computing a second set of characteristics missing form the retrieved second patient data, and adding the computed second set of characteristics to the retrieved second patient data to obtain augmented second patient data;

input the augmented first patient data into the trained machine-learning model to determine a first set of one or more risk values for the first patient;

input the augmented second patient data into the trained machine-learning model to determine a second set of one or more risk values for the second patient;

compare the first set of one or more risk values and the second set of one or more risk values to determine a priority for distributing care to the first patient and the second patient; and in accordance with the determination that the first patient has priority, generate a medical recommendation based on the priority, wherein the medical recommendation comprises an identification of a treatment for the first patient.

* * * * *